(12) United States Patent
Ohishi et al.

(10) Patent No.: US 11,327,129 B2
(45) Date of Patent: May 10, 2022

(54) MRI APPARATUS

(71) Applicant: CANON MEDICAL SYSTEMS CORPORATION, Otawara (JP)

(72) Inventors: Takafumi Ohishi, Yokohama (JP); Sadanori Tomiha, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/854,060

(22) Filed: Apr. 21, 2020

(65) Prior Publication Data

US 2020/0341083 A1  Oct. 29, 2020

(30) Foreign Application Priority Data

Apr. 24, 2019 (JP) .............................. JP2019-082561

(51) Int. Cl.
*G01R 33/341* (2006.01)
*A61B 5/055* (2006.01)
*G01R 33/36* (2006.01)

(52) U.S. Cl.
CPC ............ *G01R 33/341* (2013.01); *A61B 5/055* (2013.01); *G01R 33/3692* (2013.01)

(58) Field of Classification Search
CPC .... G01R 33/341; G01R 33/3692; A61B 5/055
See application file for complete search history.

(56) References Cited

U.S. PATENT DOCUMENTS

| | | | |
|---|---|---|---|
| 8,866,480 B2* | 10/2014 | Waffenschmidt .. | G01R 33/3692 324/318 |
| 10,466,318 B2* | 11/2019 | Zhai ................. | G01R 33/34076 |
| 2004/0030238 A1* | 2/2004 | Vaughan .............. | G01R 33/283 600/418 |
| 2007/0176601 A1* | 8/2007 | Adachi .................. | G01R 33/34 324/310 |
| 2008/0259897 A1 | 10/2008 | Van Helvoort et al. | |
| 2010/0117643 A1* | 5/2010 | Hulbert .............. | G01R 33/3621 324/307 |

(Continued)

FOREIGN PATENT DOCUMENTS

| | | | |
|---|---|---|---|
| EP | 1 770 874 A1 | 4/2007 | |
| EP | 3 413 076 A1 | 12/2018 | |

(Continued)

OTHER PUBLICATIONS

Extended European Search Report dated Aug. 24, 2020 in European Patent Application No. 20170670.2, 11 pages.

*Primary Examiner* — Dixomara Vargas
(74) *Attorney, Agent, or Firm* — Oblon, McClelland, Maier & Neustadt, L.L.P.

(57) ABSTRACT

In one embodiment, an MRI apparatus includes: an RF coil configured to receive a magnetic resonance signal from an object and include a first wireless antenna with horizontal polarization; a main body provided with a bore and configured to apply an RF pulse to an object, the bore being a space in which the object is placed during imaging; and at least one second wireless antenna configured to perform wireless communication between the RF coil and the main body via the first wireless antenna, one of the at least one second wireless antenna being disposed at an uppermost portion in an outer periphery of an opening edge of the bore.

20 Claims, 18 Drawing Sheets

(56) References Cited

U.S. PATENT DOCUMENTS

| | | | |
|---|---|---|---|
| 2010/0117652 A1 | 5/2010 | Cork et al. | |
| 2010/0119138 A1* | 5/2010 | Hulbert | G01R 33/56509 |
| | | | 382/131 |
| 2010/0253350 A1* | 10/2010 | Huish | G01R 33/3692 |
| | | | 324/318 |
| 2011/0274183 A1* | 11/2011 | Wang | H04B 7/061 |
| | | | 375/259 |
| 2012/0268116 A1* | 10/2012 | Zhu | G01R 33/3642 |
| | | | 324/307 |
| 2012/0268132 A1* | 10/2012 | Zhu | G01R 33/3692 |
| | | | 324/322 |
| 2013/0221966 A1* | 8/2013 | Zhu | G01R 33/3642 |
| | | | 324/318 |
| 2015/0253404 A1* | 9/2015 | Tomiha | G01R 33/3692 |
| | | | 324/322 |
| 2016/0077172 A1* | 3/2016 | Duensing | G01R 33/34084 |
| | | | 600/422 |
| 2018/0246179 A1* | 8/2018 | Zhai | G01R 33/3875 |
| 2018/0356478 A1* | 12/2018 | Reykowski | G01R 33/3692 |
| 2019/0170839 A1 | 6/2019 | Tomiha et al. | |
| 2020/0033429 A1 | 1/2020 | Darnell et al. | |

FOREIGN PATENT DOCUMENTS

| | | |
|---|---|---|
| JP | 2009-520556 A | 5/2009 |
| WO | WO 2018/183035 A1 | 10/2018 |

* cited by examiner $$E_t = E_{DPt} \cdot \cos\theta + E_{SLt} \cdot \sin\theta$$

MRI APPARATUS

CROSS-REFERENCE TO RELATED APPLICATION

This application is based upon and claims the benefit of priority from Japanese Patent Application No. 2019-082561, filed on Apr. 24, 2019, the entire contents of which are incorporated herein by reference.

TECHNICAL FIELD

Disclosed Embodiments relate to a magnetic resonance imaging (MRI) apparatus.

BACKGROUND

An MRI apparatus is an imaging apparatus that magnetically excites nuclear spin of an object placed in a static magnetic field by applying a radio frequency (RF) pulse having the Larmor frequency and reconstructs an image on the basis of magnetic resonance (MR) signals emitted from the object due to the excitation.

In an MRI apparatus, an RF pulse is transmitted from a whole body coil toward an object. An MR signal emitted from the object in response to this transmission is received by the whole body coil or an RF coil. The RF coil receives the MR signal emitted from the object at a position close to the object. Depending on the anatomical imaging part of the object, there are various RF coils such as for the head, for the chest, for the spine, and for the lower limbs. The RF coil is also referred to as a local coil or a surface coil.

Conventionally, a wired RF coil is often used and this RF coil is configured to transmit by wire a received MR signal to the main body of the MRI apparatus (hereinafter, the main body of the MRI apparatus is shortly referred to as the main body or the controller). In contrast, a wireless RF coil has been developed and this wireless RF coil is configured to convert the received MR signal from an analog signal to a digital signal by an AD converter and wirelessly transmit the digitized MR signal to the main body.

The RF coil is placed close to the object lying in a cylindrical examination space (i.e., so-called a bore in usual cases) formed in the gantry of the MRI apparatus. When the wireless RF coil is used, part or entirety of the space inside the bore is included in the electric-wave propagation path between the wireless RF coil and the main body. Since the electric wave propagating in the bore is affected by the reflected wave from the inner wall of the bore, a standing wave may occur in the bore.

When the standing wave occurs, a place where the received power becomes strong and a place where it becomes weak appear in the bore. Accordingly, there is a high possibility that wireless communication between the RF coil and the main body becomes unstable in the place where the received power is weak.

Thus, with respect to an MRI apparatus provided with a wireless RF coil, there is a strong demand for securing a stable wireless communication line between the wireless RF coil and the main body.

In addition to the above-described demand, there has been another demand for a technique that allows biological information such as heartbeat and respiration of an object to be readily acquired without imposing a burden on the object.

DETAILED DESCRIPTION

In one embodiment, an MRI apparatus includes: an RF coil configured to receive a magnetic resonance signal from an object and include a first wireless antenna with horizontal polarization; a main body provided with a bore and configured to apply an RF pulse to the object, the bore being a space in which the object is placed during imaging; and at least one second wireless antenna configured to perform wireless communication between the RF coil and the main body via the first wireless antenna, one of the at least one second wireless antenna being disposed at an uppermost portion in an outer periphery of an opening edge of the bore.

First Embodiment

Hereinbelow, the first embodiment of the present invention will be described by referring to the accompanying drawings.

Figure 1:
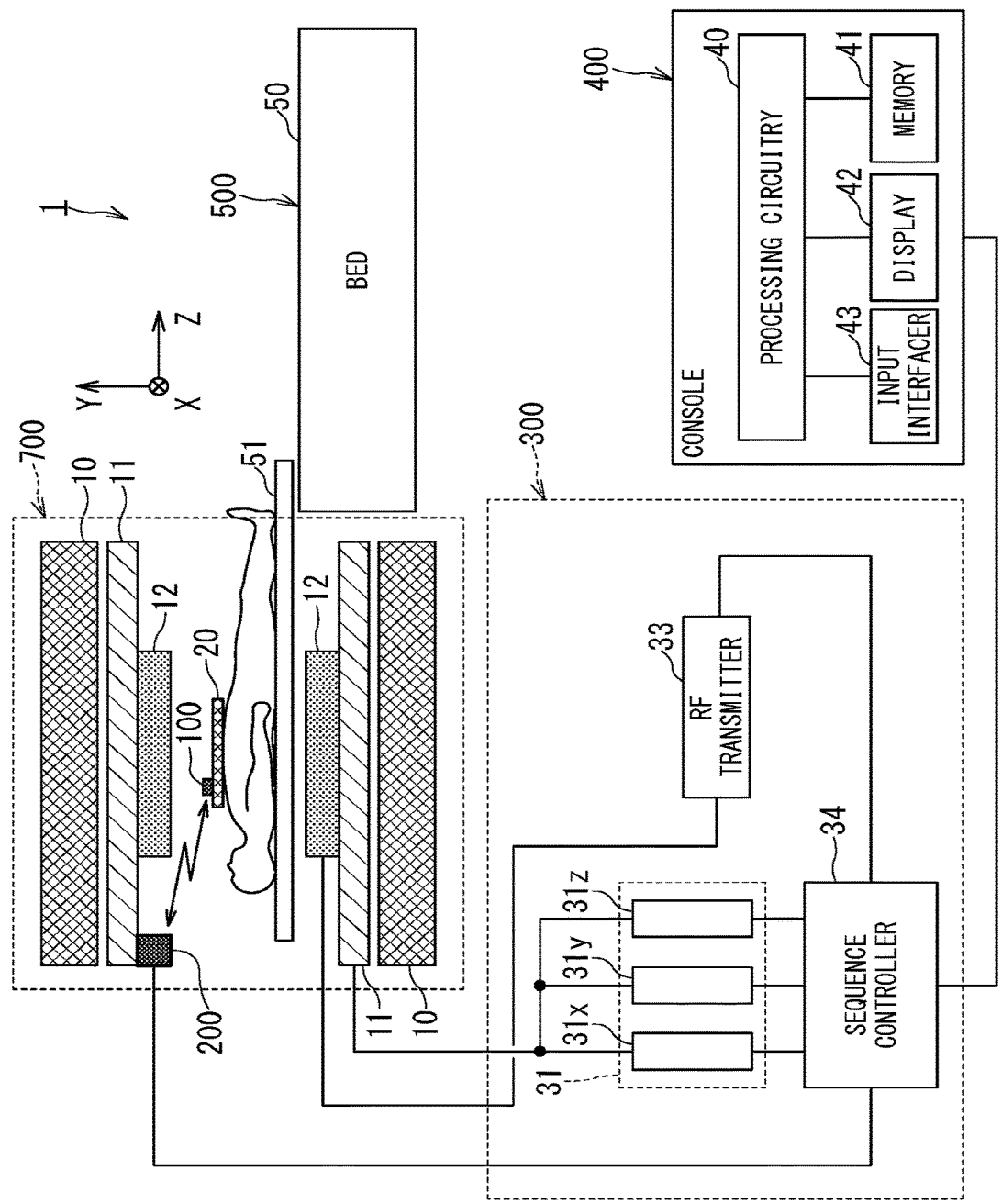
FIG. 1 is a configuration diagram illustrating an overall configuration of an MRI apparatus according to each embodiment.

FIG. 1 is a block diagram illustrating overall configuration of an MRI apparatus 1 according to the first embodiment. The MRI apparatus 1 of the first embodiment includes a gantry 700, a control cabinet 300, a console 400, and a bed 500.

The gantry 700 includes a static magnetic field magnet 10, a gradient coil 11, and a whole body (WB) coil 12, and these components are housed in a cylindrical housing. The bed 500 includes a bed body 50 and a table 51. In addition, the MRI apparatus 1 includes at least one RF coil 20 to be disposed close to the object. As described above, the RF coil 20 is also referred to as a local coil 20 or a surface coil 20.

The control cabinet 300 includes three gradient coil power supplies 31 (31x for an X-axis, 31y for a Y-axis, and 31z for a Z-axis), an RF transmitter 33, and a sequence controller 34.

The static magnetic field magnet 10 of the gantry 700 is substantially in the form of a cylinder, and generates a static magnetic field inside a bore, which is a space formed inside the cylindrical structure and serves as an imaging region of the object (for example, a patient). The gradient coil 11 is also substantially in the form of a cylinder and is fixed to the inside of the static magnetic field magnet 10. The gradient coil 11 has a three-channel structure. Each channel of the gradient coil 11 is supplied with an electric current from the corresponding gradient magnetic field power supply (31x, 31y, or 31z) such that a gradient magnetic field is generated in each of the X-axis, Y-axis, and Z-axis directions.

The bed body 50 of the bed 500 can move the table 51 in the vertical direction and in the horizontal direction. The bed body 50 moves the table 51 with an object placed thereon to a predetermined height before imaging. Afterward, when the object is imaged, the bed body 50 moves the table 51 in the horizontal direction so as to move the object to the inside of the bore.

The WB body coil 12 is shaped substantially in the form of a cylinder so as to surround the object, and is fixed to the inside of the gradient coil 11. The WB coil 12 applies RF pulses to be transmitted from the RF transmitter 33 to the object, and receives magnetic resonance (MR) signals emitted from the object due to excitation of hydrogen nuclei.

The RF transmitter 33 transmits an RF pulse to the WB coil 12 on the basis of an instruction from the sequence controller 34.

The sequence controller 34 performs a scan of the object by driving the gradient coil power supplies 31, and the RF transmitter 33, under the control of the console 400.

The sequence controller 34 includes processing circuitry (not shown). This processing circuitry is configured as, for example, a processor for executing predetermined programs or configured as hardware such as a field programmable gate array (FPGA) and an application specific integrated circuit (ASIC).

The console 400 is configured as a computer that includes processing circuitry 40, a memory 41, a display 42, and an input interface 43.

The memory 41 is a recording medium including a read-only memory (ROM) and a random access memory (RAM) in addition to an external memory device such as a hard disk drive (HDD) and an optical disc device. The memory 41 stores various programs to be executed by a processor of the processing circuitry 40 as well as various data and information.

The display 42 is a display device such as a liquid crystal display panel, a plasma display panel, and an organic EL panel.

The input interface 43 includes various devices for an operator to input various data and information, and is configured of, for example, a mouse, a keyboard, a trackball, and/or a touch panel.

The processing circuitry 40 is, for example, a circuit provided with a central processing unit (CPU) and/or a special-purpose or general-purpose processor. The processor implements various functions described below by executing the programs stored in the memory 41. The processing circuitry 40 may be configured of hardware such as the FPGA and the ASIC. The various functions described below can also be implemented by such hardware. Additionally, the processing circuitry 40 can implement the various functions by combining hardware processing and software processing based on its processor and programs.

The MRI apparatus 1 includes at least one RF coil 20 in addition to the WB coil 12. The RF coil 20 receives MR signals emitted from the object at a position close to the object. The RF coil 20 includes plural coil elements, for example. Depending on the anatomical imaging part of the object, there are various RF coils 20 such as for the head, for the chest, for the spine, for the lower limbs, and for the whole body. Of these various RF coils, FIG. 1 illustrates the RF coil 20 for imaging the chest.

The RF coil 20 of the MRI apparatus 1 is a wireless RF coil 20 and is configured to convert an MR signal received from the object into a digital signal and transmit it to an MRI main body 600 wirelessly. In the present specification, the configuration of the entire MRI apparatus 1 excluding the RF coil 20 is referred to as the MRI main body 600.

The RF coil 20 is provided with an antenna 100 for wirelessly transmitting and wirelessly receiving signals to/from the MRI main body 600. The MRI main body 600 is also provided with an antenna 200 for wirelessly transmitting and wirelessly receiving signals to/from the RF coil 20. The antenna 100 provided in the RF coil 20 is hereinafter referred to as the coil-side wireless antenna 100 (or the first wireless antenna 100). The antenna 200 provided in the MRI main body 600 is hereinafter referred to as the main-body-side wireless antenna 200 (or the second wireless antenna 200).

From the coil-side wireless antenna 100 to the main-body-side wireless antenna 200, digitized MR signals are mainly transmitted. From the main-body-side wireless antenna 200 to the coil-side wireless antenna 100, various control signals for the RF coil 20 are mainly transmitted.

As an implementation form of the coil-side wireless antenna 100, it is conceivable to connect the RF coil 20 and the coil-side wireless antenna 100 by a cable. However, from the viewpoint of convenience in handling the RF coil 20, it is more convenient that the RF coil 20 and the coil-side wireless antenna 100 are integrated without using a cable. For this reason, the coil-side wireless antenna 100 of the present embodiment adopts an implementation form in which the coil-side wireless antenna 100 is housed inside the RF coil 20 or another implementation form in which the coil-side wireless antenna 100 is mounted outside the RF coil 20.

As an implementation of the main-body-side wireless antenna 200, it is conceivable to install the main-body-side wireless antenna 200 at a position away from the gantry 700, for example, at any position in the examination room (i.e., shield room) where the gantry 700 is installed (for example, part of the inner wall of the examination room). However, in the case of such an implementation form, the electric-wave propagation environment varies depending on the layout of the examination room, and it takes time to adjust the installation position of the main-body-side wireless antenna 200. Further, even after the completion of the adjustment, it is conceivable that only a slight environmental change such as slight positional shift of any article in the examination room varies the electric-wave propagation environment to an extent that readjustment is needed. Thus, the main-body-side wireless antenna 200 of the present embodiment is installed inside the bore of the gantry 700. In particular, in the present embodiment, a plurality of the main-body-side wireless antennas 200 are provided and one of the main-body-side wireless antenna 200 is disposed at the uppermost portion (or, at the top position) in the outer periphery of the opening edge of the bore.

Figure 2:
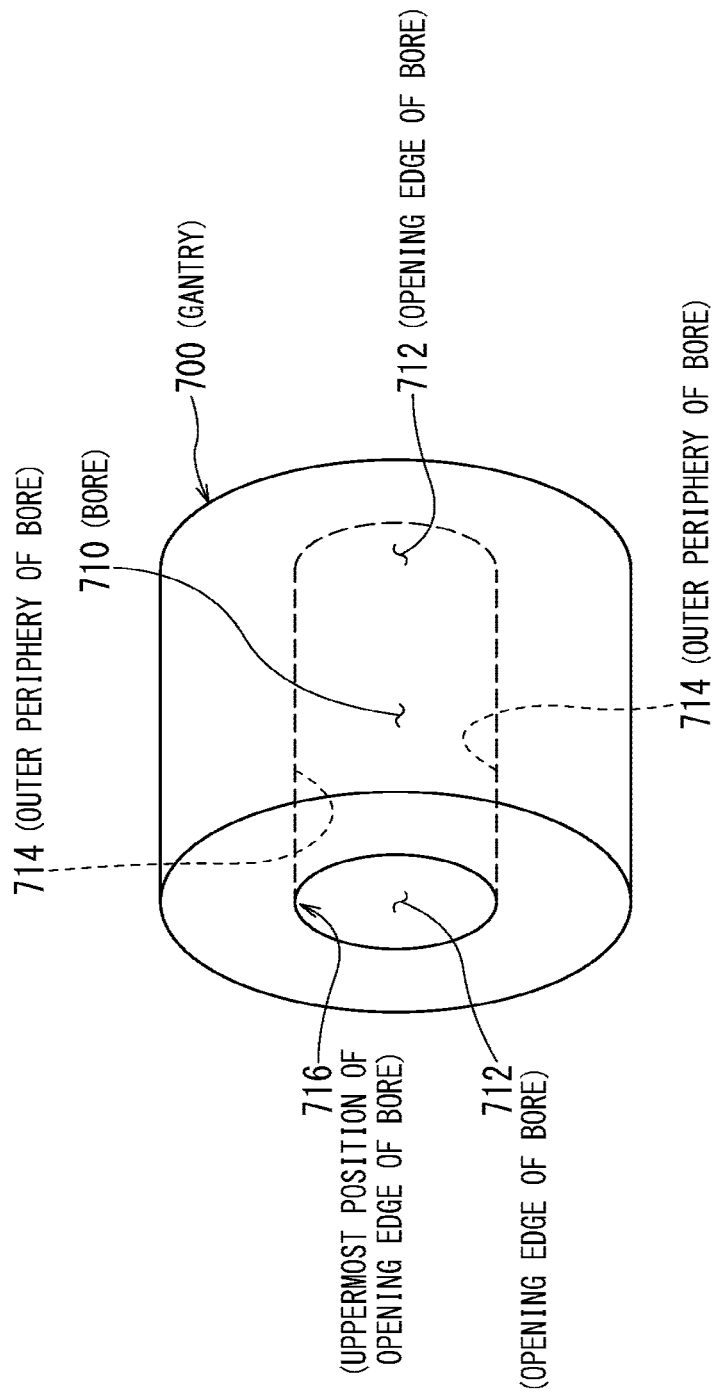
FIG. 2 is a schematic diagram for defining terms related to positions in or around the bore of the MRI apparatus as used in the present Specification.

FIG. 2 is a schematic diagram for defining terms related to positions in or around the bore as used in this Specification. As described above, the gantry 700 includes the static magnetic field magnet 10, the gradient coil 11, the WB coil 12, and these components are housed in the housing, the interior of which is cylindrically formed. A substantially columnar space formed by this housing, the interior of which is cylindrically formed, is called the bore 710. Thus, the outer periphery 714 of the bore 710 matches the inner periphery of the cylindrical housing inside the gantry 700.

The bore 710 has a cylindrical shape, and a circular opening is formed at each of both ends of the cylindrical shape. This circular opening is called the opening edge 712 of the bore 710. Further, the uppermost position of the opening edge 712 of the bore 710 is referred to as the uppermost position 716, or as the bore-end uppermost position 716.

For the avoidance of doubt, it should be noted that the terms "upper" and "lower" are understood with respect to an apparatus oriented such that a table positioned in the bore faces upwards.

(Coil-Side Wireless Antenna)

Figure 3A:
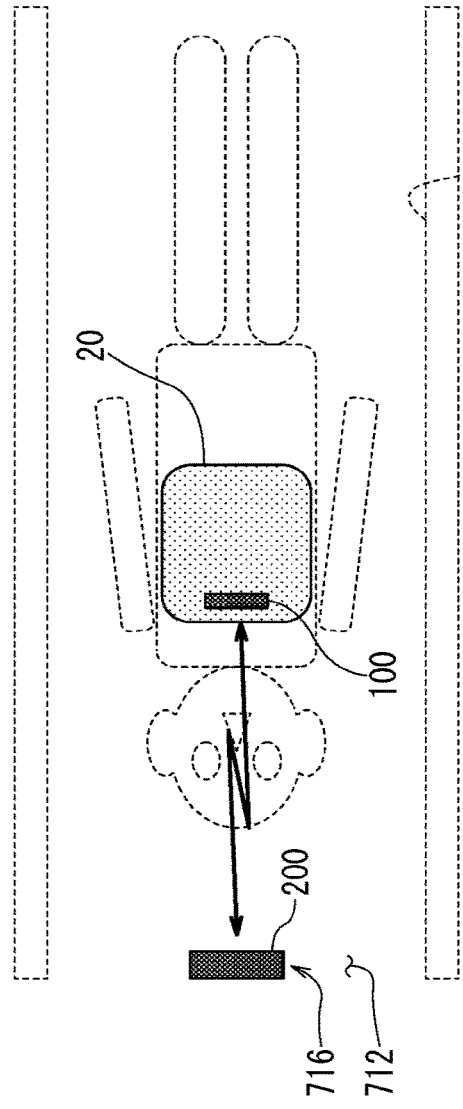
FIG. 3A and FIG. 3B are schematic diagrams illustrating positional relationship between a coil-side wireless antenna and a main-body-side wireless antenna.
Figure 3B:
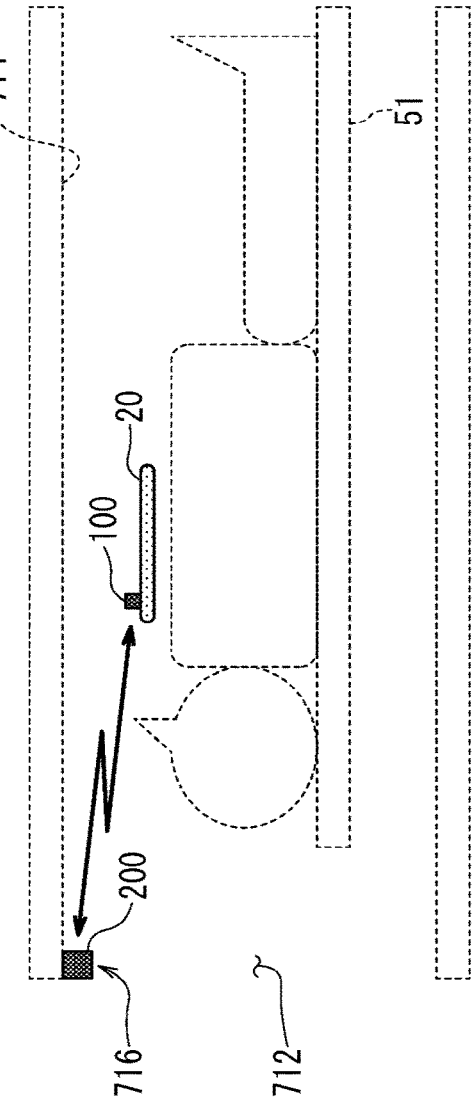

FIG. 3A and FIG. 3B are schematic diagrams for illustrating positional relationship between the coil-side wireless antenna 100 and one of the main-body-side wireless antennas 200, and also for illustrating orientation of the two antennas.

Figure 4:
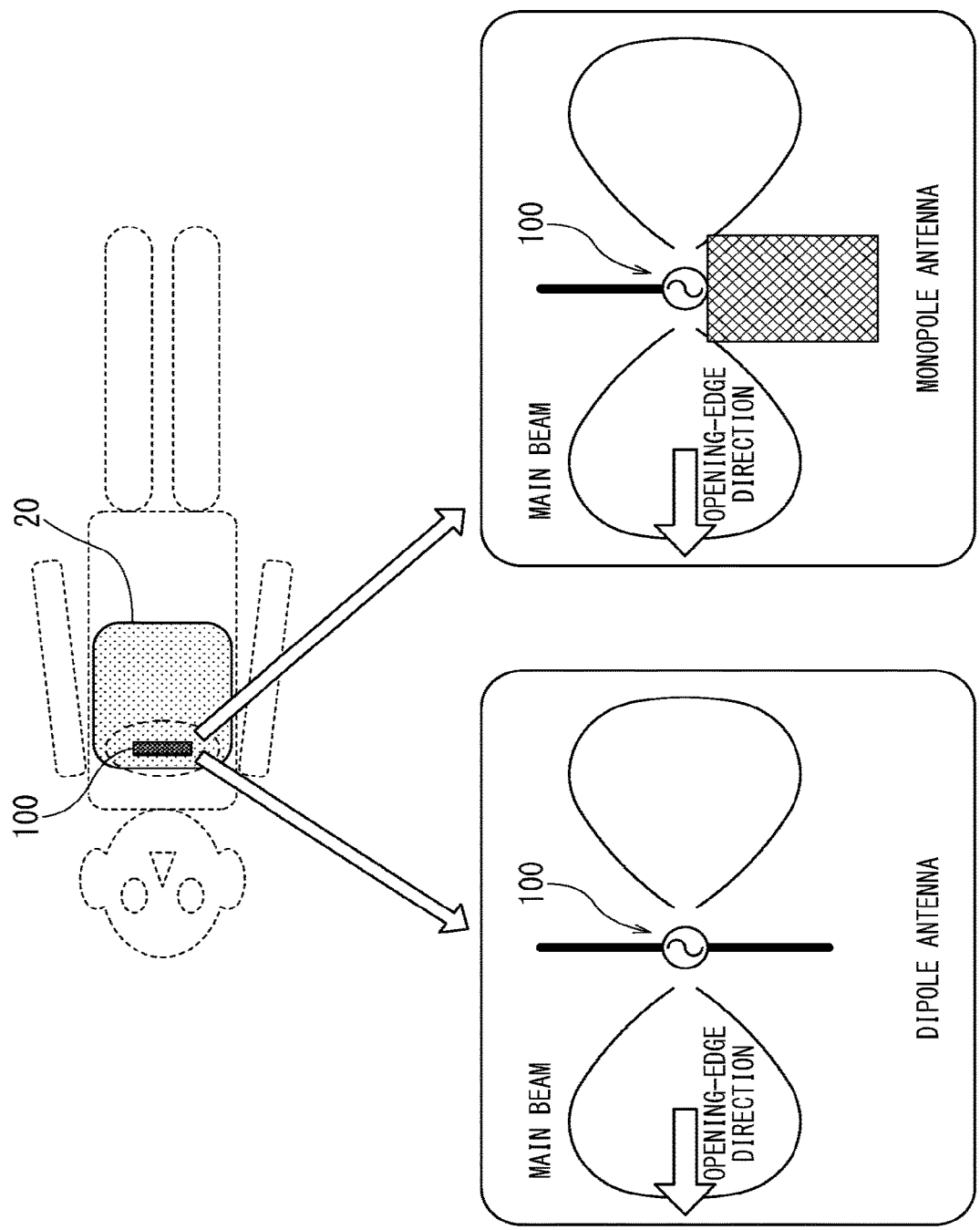
FIG. 4 is a schematic diagram illustrating arrangement, orientation, and type of the coil-side wireless antenna.

FIG. 4 is also a schematic diagram, in particular, for illustrating disposition, orientation, and type of the coil-side wireless antenna 100.

As shown in FIG. 4, in the present embodiment, a linear antenna such as a dipole antenna or a monopole antenna is used as the coil-side wireless antenna 100. Such a linear antenna can be mounted or accommodated along the main face of the RF coil 20. In other words, when the longitudinal direction of the elements of the dipole antenna or the monopole antenna are horizontally arranged, the antenna can be accommodated inside the RF coil 20 without protruding from the RF coil 20, or can be mounted along the outer peripheral face of the RF coil 20. Further, since such a linear antenna can be disposed at the end of the RF coil 20, the detection function of the coil elements in the RF coil 20 is not impaired. Note that the polarization of each of the dipole antenna or and the monopole antenna is a linear polarization. Thus, when the respective elements of the dipole antenna or the monopole antenna are arranged such that the longitudinal direction of these elements are along the horizontal direction, the polarization of the coil-side wireless antenna 100 leads to a horizontal polarization.

Further, by disposing the dipole antenna or the monopole antenna such that the longitudinal direction of the horizontally arranged dipole antenna element or the monopole antenna element becomes coincident with the left-right direction of the subject (for example, a human body), in other words, by disposing the dipole antenna or the monopole antenna such that the longitudinal direction of the horizontally arranged dipole antenna element or the monopole antenna element becomes orthogonal to the longitudinal direction of the bore 710, the main beam direction of the dipole or monopole antenna can be directed toward the open edge 712 of the bore. As a result, the strength of the wireless signal between the coil-side wireless antenna 100 and the main-body-side wireless antenna 200 disposed at the bore-end uppermost position 716 can be increased.

The main-body-side wireless antenna 200 is disposed at the bore-end uppermost position 716 as shown in FIG. 3. As described below, a plurality of main-body-side wireless antennas 200 can be arranged along the outer periphery of the opening edge 712 of the bore. Also in this case, it is preferred that one of the main-body-side wireless antennas 200 is disposed at the bore-end uppermost position 716.

When the main-body-side wireless antenna 200 is configured as a dipole antenna similarly to the coil-side wireless antenna 100, and when the coil elements of this dipole antenna are arranged parallel to the opening plane of the bore and along the outer periphery of the opening edge 712 of the bore, the polarization of the dipole antenna becomes a horizontal polarization by disposing this dipole antenna at the bore-end uppermost position 716. As a result, the polarization of the main-body-side wireless antenna 200 and the coil-side wireless antenna 100 coincides with each other as horizontally polarized waves, and thus signal loss due to polarization mismatch can be avoided.

Figure 5A:
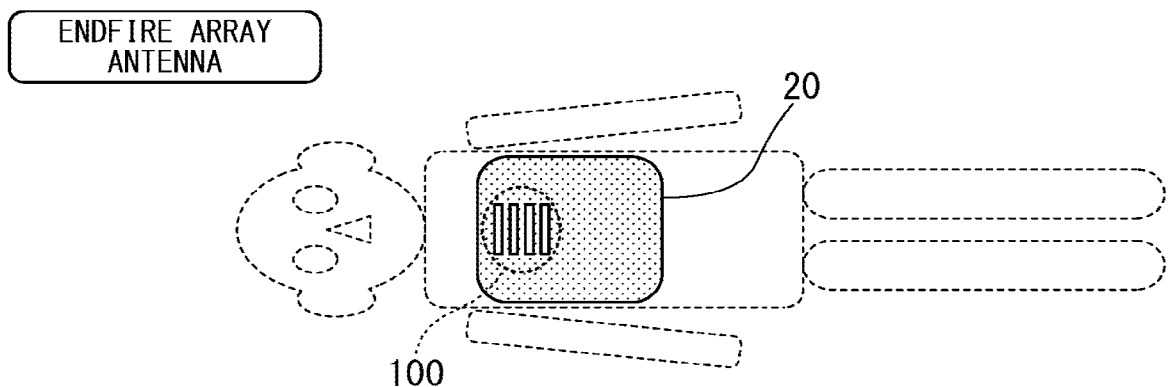
FIG. 5A and FIG. 5B are schematic diagrams illustrating other aspects of the coil-side wireless antenna.
Figure 5B:
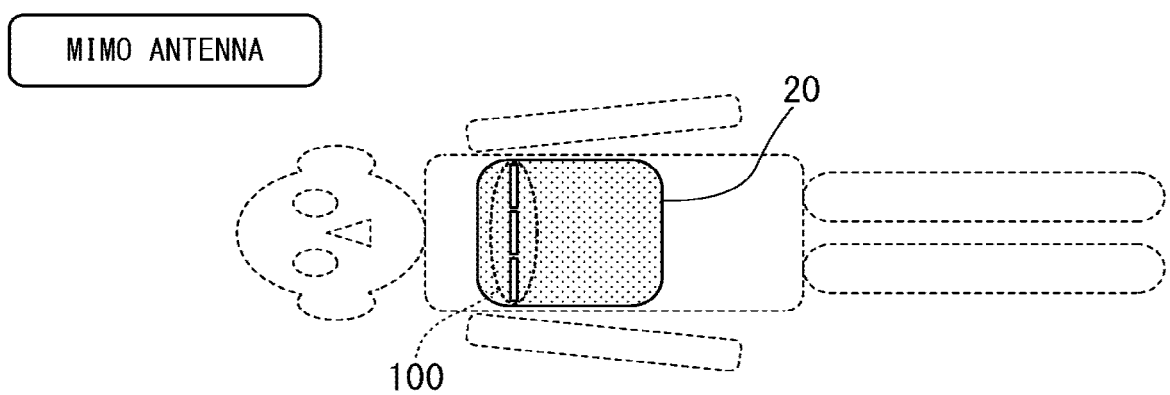

FIG. 5A and FIG. 5B are schematic diagrams illustrating other aspects of the coil-side wireless antenna 100.

As shown in FIG. 5A, the coil-side wireless antenna 100 can be configured as an endfire array antenna. An endfire array antenna is an antenna that includes a plurality of antenna elements arranged as a linear array and is adjusted in phase between the antenna elements and at intervals between the respective antenna elements so as to generate a main lobe in the direction of the array axis (i.e., the direction called the endfire direction). When the endfire array antenna is used, the main lobe having stronger directivity can be directed toward the opening edge 712 of the bore as compared with a single dipole antenna.

Alternatively, as shown in FIG. 5B, when a plurality of the coil-side wireless antennas 100 are arranged in the left and right direction of the object, the standing wave environment can be changed by a directivity control in the left and right direction, and thus, a radio wave environment with good communication quality can be obtained.

The plurality of the coil-side wireless antennas 100 may be configured as a MIMO (Multiple-Input and Multiple-Output) antenna. The MIMO antenna literally includes a plurality of the coil-side wireless antennas 100 and a plurality of the main-body-side wireless antennas 200. The MIMO antenna, however, may be replaced by a MISO (Multiple Input and Single Output) antenna, in which either a coil-side wireless antenna assembly or a main-body-side antenna assembly, for example, only a plurality of the coil-side wireless antennas 100 are included.

Figures 6A, 6B:
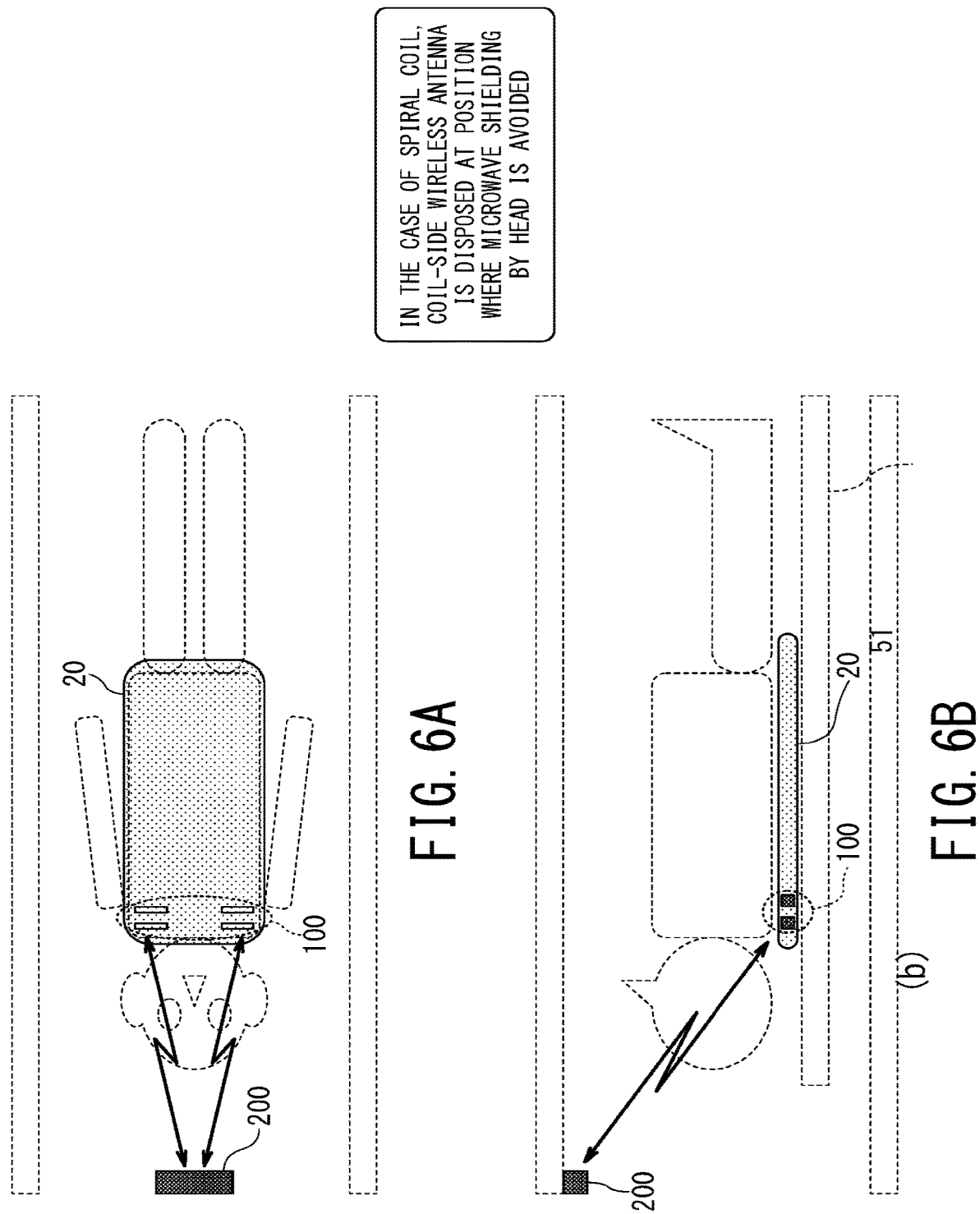
FIG. 6A and FIG. 6B are schematic diagrams illustrating the coil-side wireless antenna when the RF coil is a spine coil.

FIG. 6A and FIG. 6B are schematic diagrams illustrating the coil-side wireless antenna 100 for the RF coil 20 as a spine coil. The spine coil is usually disposed between the table 51 and the object. Thus, when the coil-side wireless antenna 100 is disposed at the center of the end of the RF coil 20 similarly to the case of the chest coil, there is a possibility that electric waves are shielded by the head of the object. Thus, as shown in FIG. 6A and FIG. 6B, the coil-side wireless antenna 100 used for the spine coil is disposed at a position where electric waves are not shielded by the head of the object. For example, inside the spine coil, the coil-side wireless antenna 100 is disposed at each of the right and left corners in the end close to the head of the object.

(Main-Body-Side Wireless Antenna)

FIG. 7A to FIG. 11C are schematic diagrams illustrating the structure and configuration of the main-body-side wireless antennas 200 of the present embodiment. The main-body-side wireless antenna 200 of the present embodiment can be configured with only a dipole antenna. However, from the viewpoint of adaptability to various polarization directions depending on the electric-wave propagation environment inside the bore, the main-body-side wireless antenna 200 is configured as a polarization diversity antenna in the present embodiment.

Figure 7A:
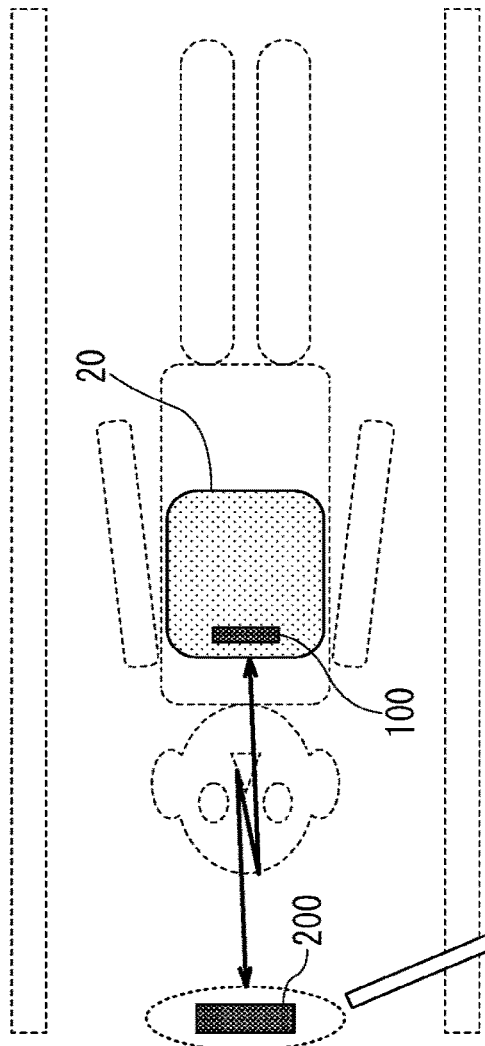
FIG. 7A and FIG. 7B are schematic diagrams illustrating structure of the main-body-side wireless antenna configured as a polarization diversity antenna.
Figure 7B:
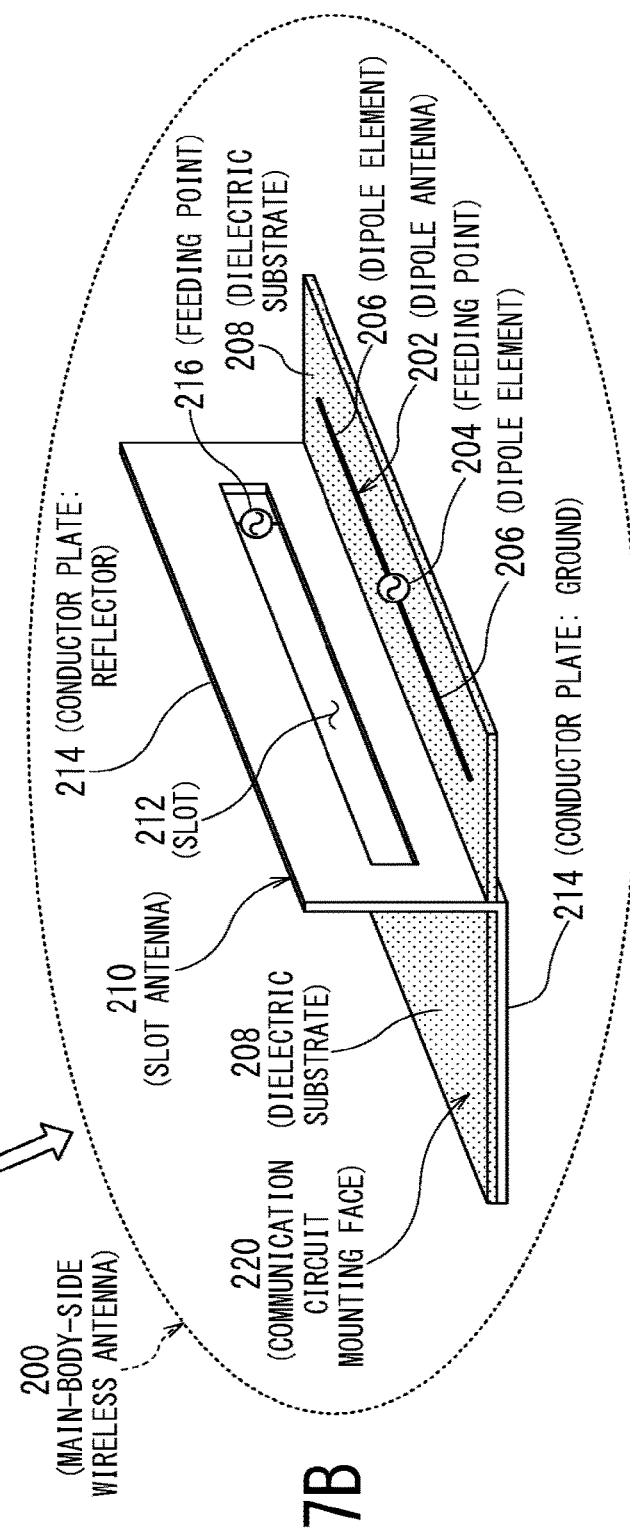

FIG. 7B is a perspective view illustrating a structure of the main-body-side wireless antenna 200 configured as a polarization diversity antenna. This main-body-side wireless antenna 200 includes a dipole antenna 202 and a slot antenna 210 such that the dipole antenna 202 and the slot antenna 210 are arranged in parallel and side-by-side.

The dipole antenna 202 is, for example, a half-wave dipole antenna and includes a feeding point 204 disposed at the center thereof and two dipole elements 206 that extend from the feeding point 204 toward the right and left. The dipole antenna 202 is disposed on a dielectric substrate 208. Additionally or alternatively, a conductor pattern corresponding to the dipole elements 206 of the dipole antenna 202 may be formed on the mounting surface of the dielectric substrate 208.

The slot antenna 210 is configured by forming a half-wavelength elongated hole (i.e., slot 212) in a conductor plate 214 that intersects the dielectric substrate 208 substantially perpendicularly. It is preferred that the feeding point 216 of the slot antenna 210 is located at a position shifted from the center in terms of impedance matching.

The direction of the electric field of the dipole antenna 202 is parallel to the longitudinal direction of the dipole elements 206. The direction of the electric field of the slot antenna 210 is orthogonal to the longitudinal direction of the slot 212. Thus, as shown in FIG. 7B, when the dipole elements 206 of the dipole antenna 202 and the slot 212 of the slot antenna 210 are arranged in parallel and side-by-side, the electric field of the dipole antenna 202 and the electric field of the slot antenna 210 are orthogonal to each other. In other words, the respective polarization planes of the dipole antenna 202 and the slot antenna 210 are orthogonal to each other, which is convenient for forming a polarization diversity antenna.

In the main-body-side wireless antenna 200 of the present embodiment, the dipole antenna 202 and the slot antenna 210 are close to each other, and the dipole antenna 202 is disposed closer to the center of the bore 710 than the slot antenna 210 (i.e., disposed closer to the coil-side wireless antenna 100). This disposition enables the conductor plate 214 of the slot antenna 210 to be used as a reflector of the dipole antenna 202 and can enhance the directivity of the dipole antenna 202 toward the coil-side wireless antenna 100.

The slot antenna 210 may be provided with a cavity resonator. When the cavity resonator is disposed at a position opposite to the coil-side wireless antenna 100, the directivity of the slot antenna 210 toward the coil-side wireless antenna 100 can be enhanced.

As shown in FIG. 7B, the main-body-side wireless antenna 200 may be configured such that the dielectric substrate 208 is extended from the position of the dipole antenna 202 to the opposite side beyond the conductor plate 214 and the conductor plate 214 of the slot antenna 210 is bent and extended on the back face of this extended dielectric substrate 208. In such a configuration, the surface extending to the opposite side of the coil-side wireless antenna 100 can be used as the mounting surface 220 of the communication circuit communicating with the main-body-side wireless antenna 200, and a compact wireless communication device with high mounting efficiency can be provided.

Figure 8:
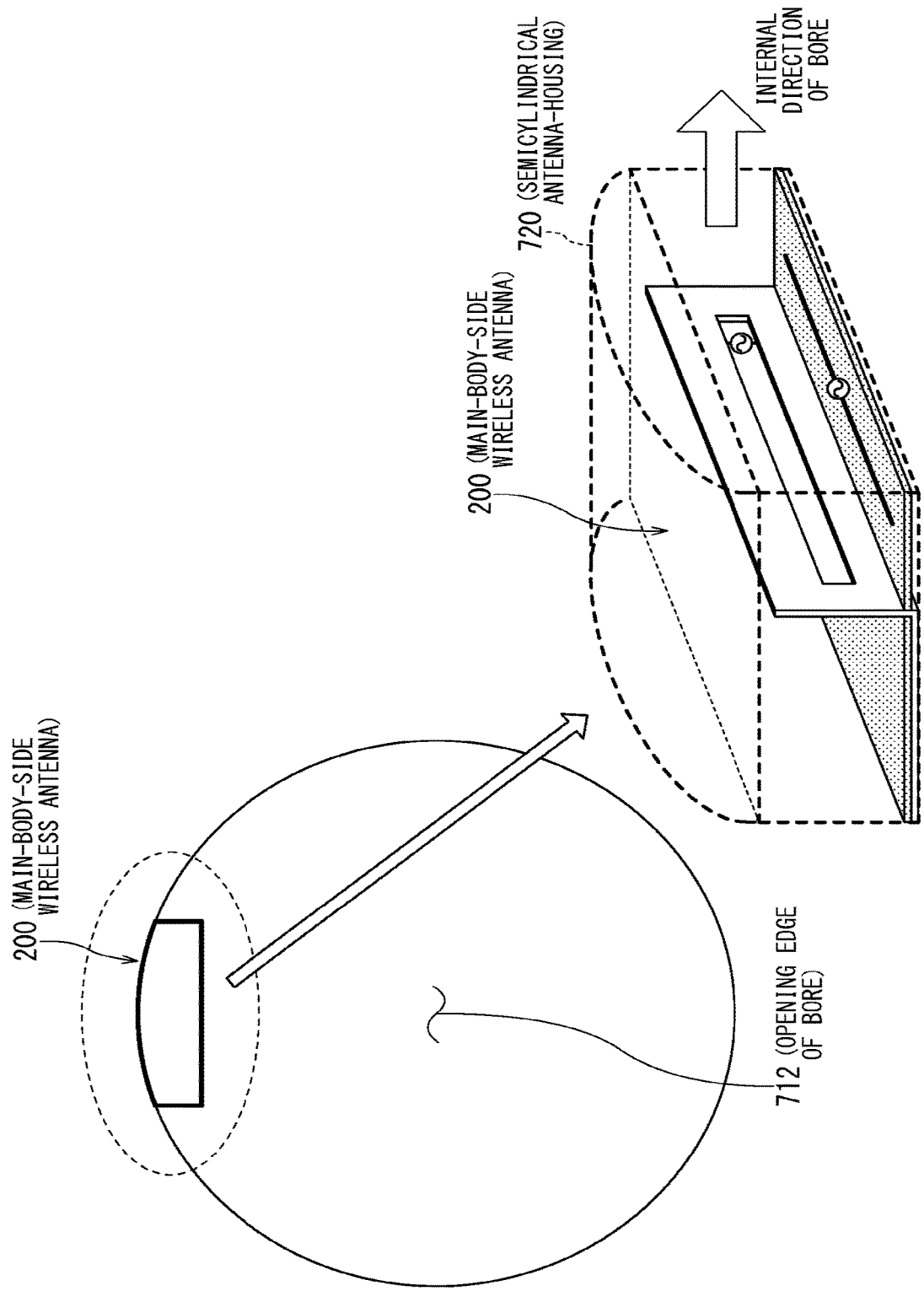
FIG. 8 is a schematic diagram illustrating an antenna-housing that houses the main-body-side wireless antenna.

FIG. 8 is a schematic diagram illustrating an antenna-housing 720 that houses the main-body-side wireless antenna 200. The antenna housing 720 is formed in a substantially semi-cylindrical shape, and one curved lateral face of the housing (i.e., the face opposite to the dielectric substrate 208) is formed in an arc shape so as to match the shape of the outer peripheral face of the cylindrical bore 710. Such a shape of the antenna housing 720 can enhance the utilization efficiency of the space of the opening edge 712 of the bore.

So far, the structure and configuration of one main-body-side wireless antenna 200 to be disposed at the opening edge 712 of the bore has been described. In the present embodiment, a plurality of such main-body-side wireless antennas 200 are disposed on the outer periphery of the opening edge 712 of the bore, and thus the quality of wireless communication between the RF coil 20 and the MRI main body 600 can be further enhanced.

Figure 9A:
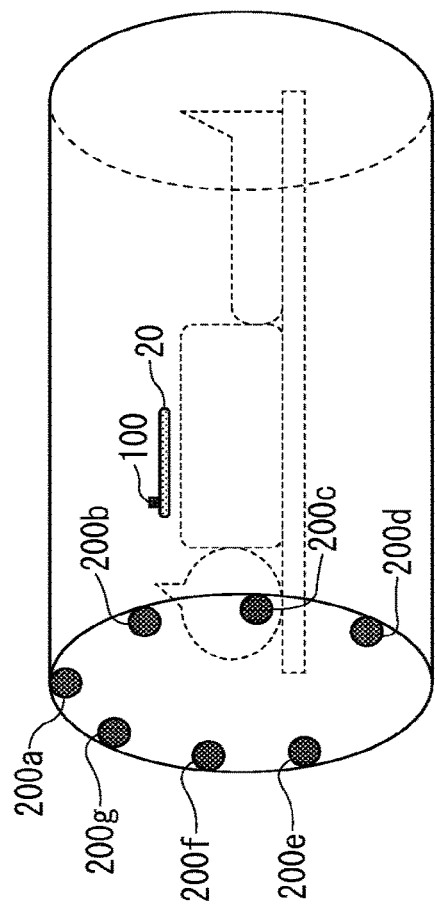
FIG. 9A to FIG. 9C are schematic diagrams illustrating a case where a plurality of main-body-side wireless antennas are arranged on the outer periphery of the opening edge of the bore.

FIG. 9A is a schematic perspective view of the gantry 700 for illustrating a first arrangement in which the plurality of the main-body-side wireless antennas 200 are arranged on the outer periphery of the opening edge 712 of the bore. FIG. 9B is a schematic diagram of the first arrangement when viewed from the outside of the bore 710. In FIG. 9A and FIG. 9B, each of the black circles 200a to 200g shown on the outer periphery of the opening edge 712 of the bore is the main-body-side wireless antenna 200 shown in FIG. 7A, FIG. 7B, or FIG. 8.

As shown in FIG. 9A and FIG. 9B, one main-body-side wireless antenna 200a is disposed at the bore-end uppermost position 716. As described above, when one of the main-body-side wireless antennas 200a to 200g is disposed at the bore-end uppermost position 716, the polarization of the dipole antenna 202 of the main-body-side wireless antenna (200a) can be set to a horizontal polarization. As a result, the polarization direction of the coil-side wireless antenna 100 and the polarization direction of the dipole antenna 202 of the main-body-side wireless antenna 200a can be matched, and signal loss due to polarization mismatch can be avoided.

Additionally or alternatively, a space diversity antenna can be configured by one main-body-side wireless antenna 200a disposed at the bore-end uppermost position 716 and a plurality of the main-body-side wireless antennas 200b to 200g arranged at the outer periphery excluding the bore-end uppermost position 716. When a standing wave is generated by the electric-wave propagation environment in the bore 710, signal intensity varies depending on the position of the main-body-side wireless antenna 200 and there are a position where the signal intensity is weak (for example, a null point) and a position where the signal intensity is strong. Even in such a case, when the space diversity antenna is configured by a spatial diversity method of selecting the antenna with strong signal intensity from among the main-body-side wireless antennas 200a to 200g arranged on the outer periphery of the opening edge 712 of the bore, or by another spatial diversity method of combining the respective signals from the main-body-side wireless antennas 200a to 200g, stable communication quality can be ensured.

Further, the main-body-side wireless antennas 200b to 200g, except the antenna 202a disposed at the bore-end uppermost position 716, are disposed in a left-right asymmetric manner. That is, the main-body-side wireless antennas 200b to 200g may be disposed asymmetrically with respect to the chain line shown in FIG. 9B. Even when the standing wave distribution becomes symmetric right and left, stable communication quality can be ensured by such asymmetric disposition of the main-body-side wireless antennas 200b to 200g and the above-described spatial diversity method.

Figure 9C:
Figure 9B:
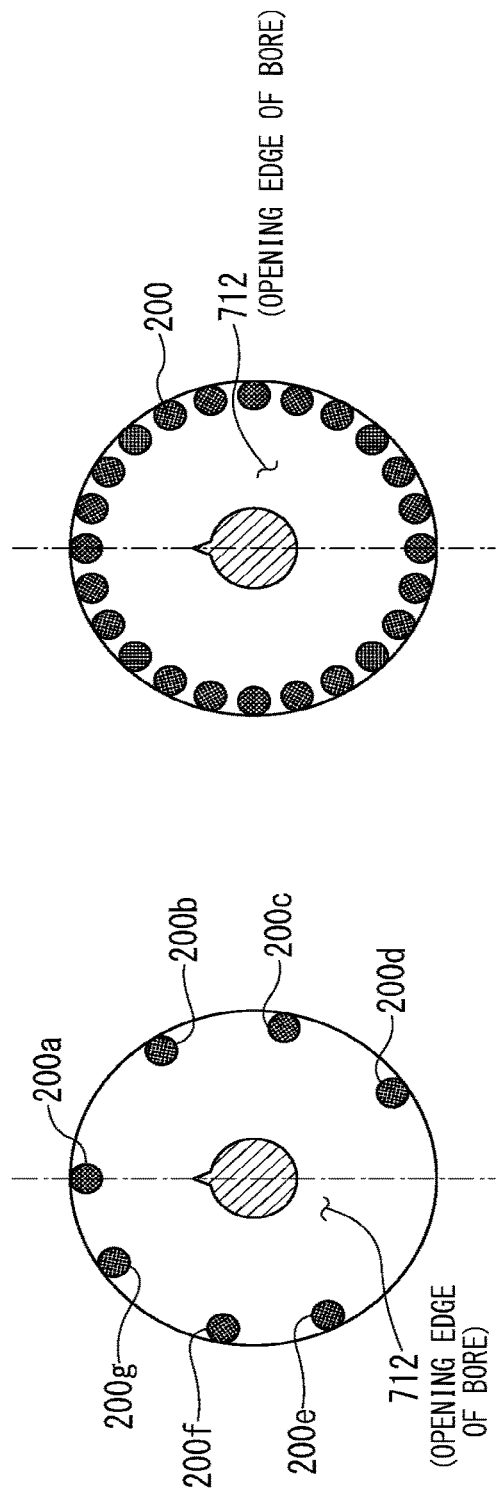

Alternatively, as shown in FIG. 9C, it may be configured such that a plurality of the main body side wireless antennas 200 are arranged at equal intervals (for example, at intervals of ½ wavelength) on the outer periphery starting from the one disposed at the bore-end uppermost position 716, and one or more antennas may be selected from these antennas on the basis of a determination criterion such as signal strength.

In order to obtain the effect of spatial diversity, it is preferred to set the arrangement interval of the respective antennas to a value larger than ½ wavelength that is the interval of standing waves. For example, assuming that the frequency of wireless communication between the RF coil 20 and the MRI main body 600 is a 2.4 GHz band, the half wavelength is about 6 centimeters. Alternatively, assuming that the frequency of wireless communication between the RF coil 20 and the MRI main body 600 is, for example, a 5 GHz band, the half wavelength is about 2.5 to 3 centimeters. In either case, it is physically possible to arrange the respective antennas at intervals of more than half wavelength in terms of spatial size of the bore, and thus the effect of spatial diversity can be obtained.

The coil-side wireless antenna 100 is configured as a dipole antenna or a monopole antenna as described above, and the electric wave to be radiated from the coil-side wireless antenna 100 is a horizontally polarized wave. The electric wave radiated from the coil-side wireless antenna 100 is affected by the reflection from the cylindrical wall of the outer periphery 714 of the bore and/or the object and the RF coil 20, which are placed in the bore 710. This reflection may deviate the polarization direction of the electric wave radiated from the coil-side wireless antenna 100 from the horizontal direction, although the main component of the polarized wave is expected to be the horizontally polarized wave. In this case, if the main body side radio antennas 200 disposed at positions other than the bore-end uppermost position 716 have only the dipole antenna 202, polarization mismatch may occur.

Figure 10A:
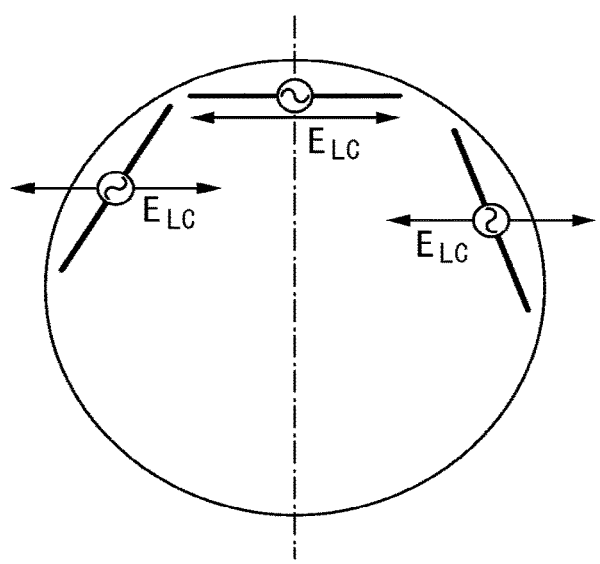
FIG. 10A and FIG. 10B are schematic diagrams illustrating a state of polarization mismatch (i.e., antenna polarization mismatch or mismatch of a polarized wave)
Figure 10B:
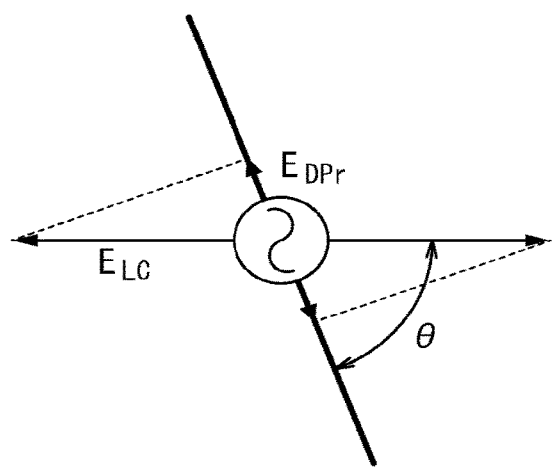

FIG. 10A and FIG. 10B are schematic diagrams illustrating the situation of the above-described polarization mismatch. In FIG. 10A and FIG. 10B, the received electric field from the coil-side wireless antenna 100 at the opening edge 712 of the bore is assumed to be a horizontal polarization. This received electric field is denoted as $E_{LC}$, and the inclination angle of the main-body-side wireless antenna 200 with respect to the horizontal direction is denoted as θ. The received electric field of the main-body-side wireless antenna 200, i.e., the received electric field of the dipole antenna 202 is denoted as $E_{DPr}$.

In this case, in each of the two main-body-side radio antennas 200 disposed farthest from the origin in the Y-axis direction (i.e., in the right-left direction) at the opening edge 712 of the bore, the longitudinal direction of the dipole antenna 202 becomes the vertical direction and the received electric field and the received power may be zero.

In order to avoid such a problem, in the present embodiment, each main-body-side wireless antenna 200 is configured as a polarization diversity antenna that includes the dipole antenna 202 and the slot antenna 210 as described above.

Figure 11A:
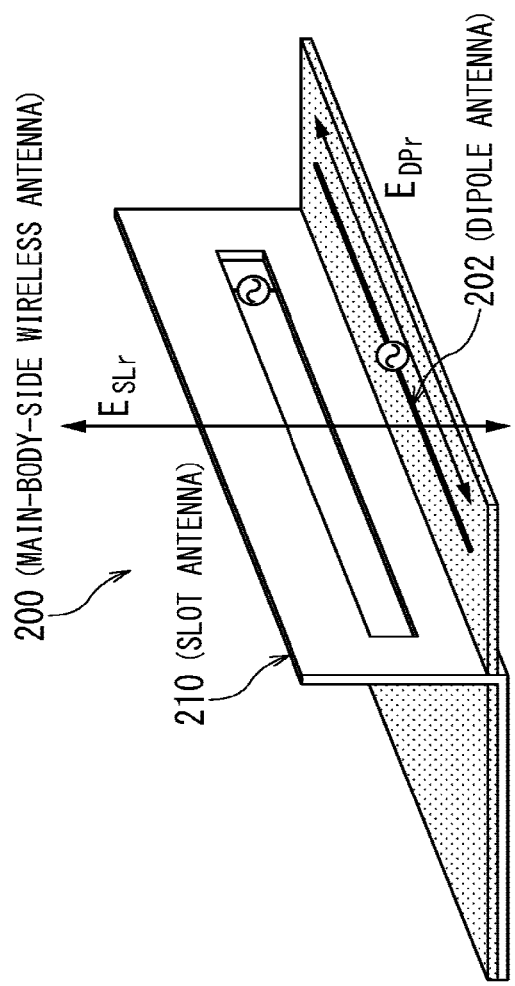
FIG. 11A to FIG. 11C are schematic diagrams illustrating the effect of a polarization diversity antenna at the time of reception.
Figure 11C:
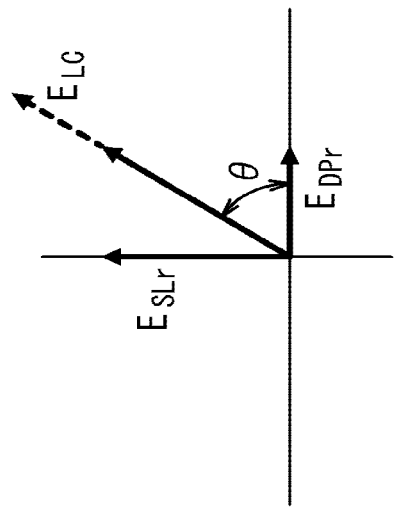
Figure 11B:
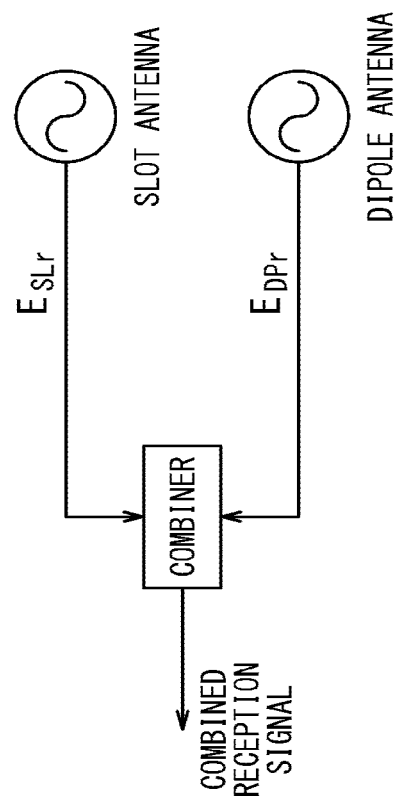

FIG. 11A to FIG. 11C are schematic diagrams illustrating the effect of the polarization diversity antenna of the present embodiment. As shown in FIG. 11A, the received electric field $E_{DPr}$ of the dipole antenna 202 is orthogonal to the received electric field $E_{SLr}$ of the slot antenna 210. Thus, as shown in FIG. 11C, regardless of the value of polarization-angle difference θ between the received electric field $E_{DPr}$ of the dipole antenna 202 and the received electric field $E_{LC}$ from the coil-side wireless antenna 100 at the opening edge 712 of the bore, the respective reception signals of the dipole antenna 202 and the slot antenna 210 never become zero at the same time, and thus the signal can be received by either antenna.

Hence, it can be configured as a polarization diversity antenna in which the signal having the larger signal strength is selected from the respective reception signals of the dipole antenna 202 and the slot antenna 210. Additionally or alternatively, as shown in FIG. 11B, it can be configured as a polarization diversity antenna that combines the respective outputs of the dipole antenna 202 and the slot antenna 210 by, for example, power addition. When the respective output powers of the dipole antenna 202 and the slot antenna 210 are combined together, a constant received power can be obtained regardless of the polarization angle difference θ.

Figure 12A:
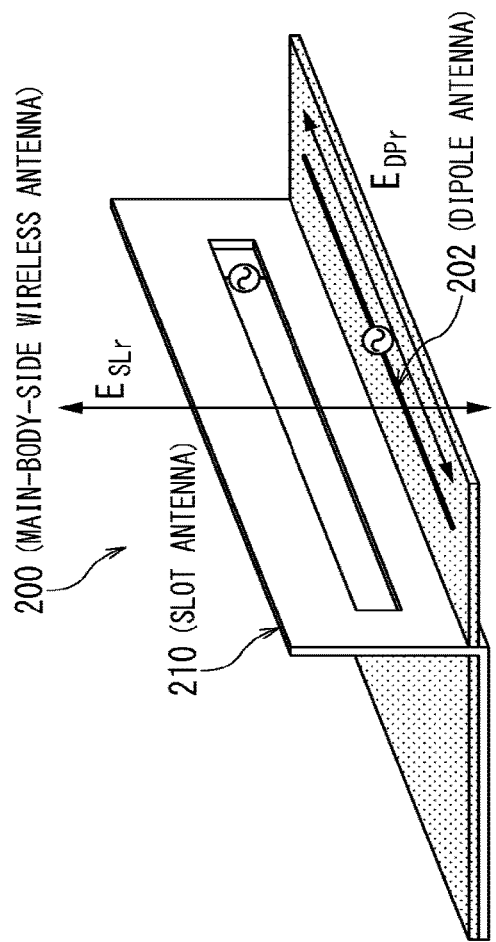
FIG. 12A to FIG. 12C are schematic diagrams illustrating polarization diversity at the time of transmission.
Figure 12B:
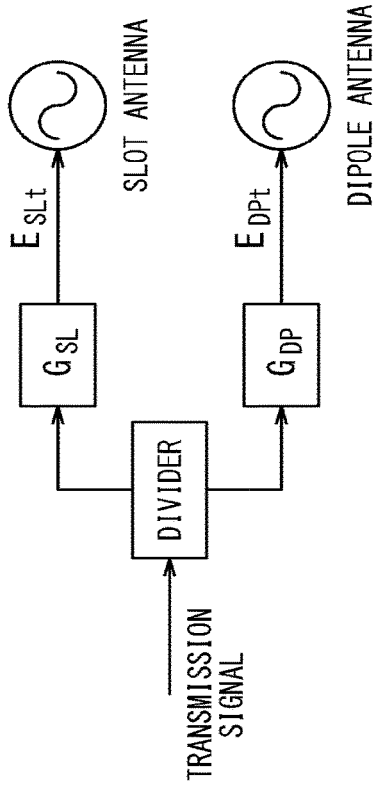
Figure 12C:
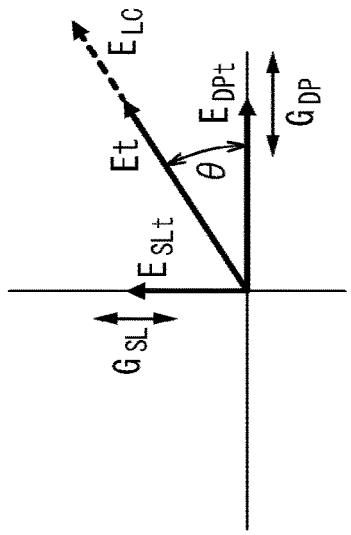

FIG. 11A to FIG. 11C illustrate the polarization diversity of the main-body-side wireless antenna 200 when receiving. FIG. 12A to FIG. 12C illustrate the polarization diversity of the main-body-side wireless antenna 200 when transmitting.

When transmitting, as shown in FIG. 12B, the transmission signal inputted to the main-body-side wireless antenna 200 is equally divided by a divider. Afterward, the divided signal for the slot antenna 210 is weighted by $G_{SL}$ and the divided signal for the dipole antenna 202 is weighted by $G_{DP}$ such that the weighted electric field $E_{SLt}$ is outputted from the slot antenna 210 and the weighted electric field $E_{DPt}$ is outputted from the dipole antenna 202. Under such a configuration, as shown in FIG. 12C, the polarization direction θ of the main-body-side wireless antenna 200 to be combined in space (i.e., the polarization direction with reference to the polarization direction of the dipole antenna 202) can be set to a desired value by adjusting the weight $G_{SL}$ for the slot antenna 210 and the weight $G_{DP}$ for the dipole antenna 202.

Consequently, for example, even when the polarization direction of the main-body-side wireless antenna 200 installed at the bore-end uppermost position 716 and the polarization direction of the coil-side wireless antenna 100 change depending on the electric-wave propagation environment inside the bore 710, the polarization direction of the transmission wave can be adjusted so as to match the polarization direction at the position of the coil-side wireless antenna 100 on the reception side.

The weight $G_{DP}$ (first weight) for the dipole antenna 202 and the weight $G_{SL}$ (second weight) for the slot antenna 210 are determined, by using reversible nature of antenna, such that (i) each main-body-side wireless antenna 200 receives the signal from the coil-side wireless antenna 100 at the installation position of each main-body-side wireless antenna 200 and (ii) the weighted combined signal of the respective reception signals of the dipole antenna 202 and the slot antenna 210 is maximized.

Second Embodiment

The RF coil 20 of the first embodiment receives the MR signals of the object by the coil elements in the RF coil 20, digitizes the received MR signals, and wirelessly transmits them to the MRI main body 600. The RF coil 20 of the second embodiment additionally includes a biological information monitor that detects biological information of the object, for example, biological information such as heartbeat and/or respiratory motion. The RF coil 20 according to the second embodiment is configured to wirelessly transmit the biological information detected by the biological information monitor to the MRI main body 600 together with the MR signals.

Figure 13:
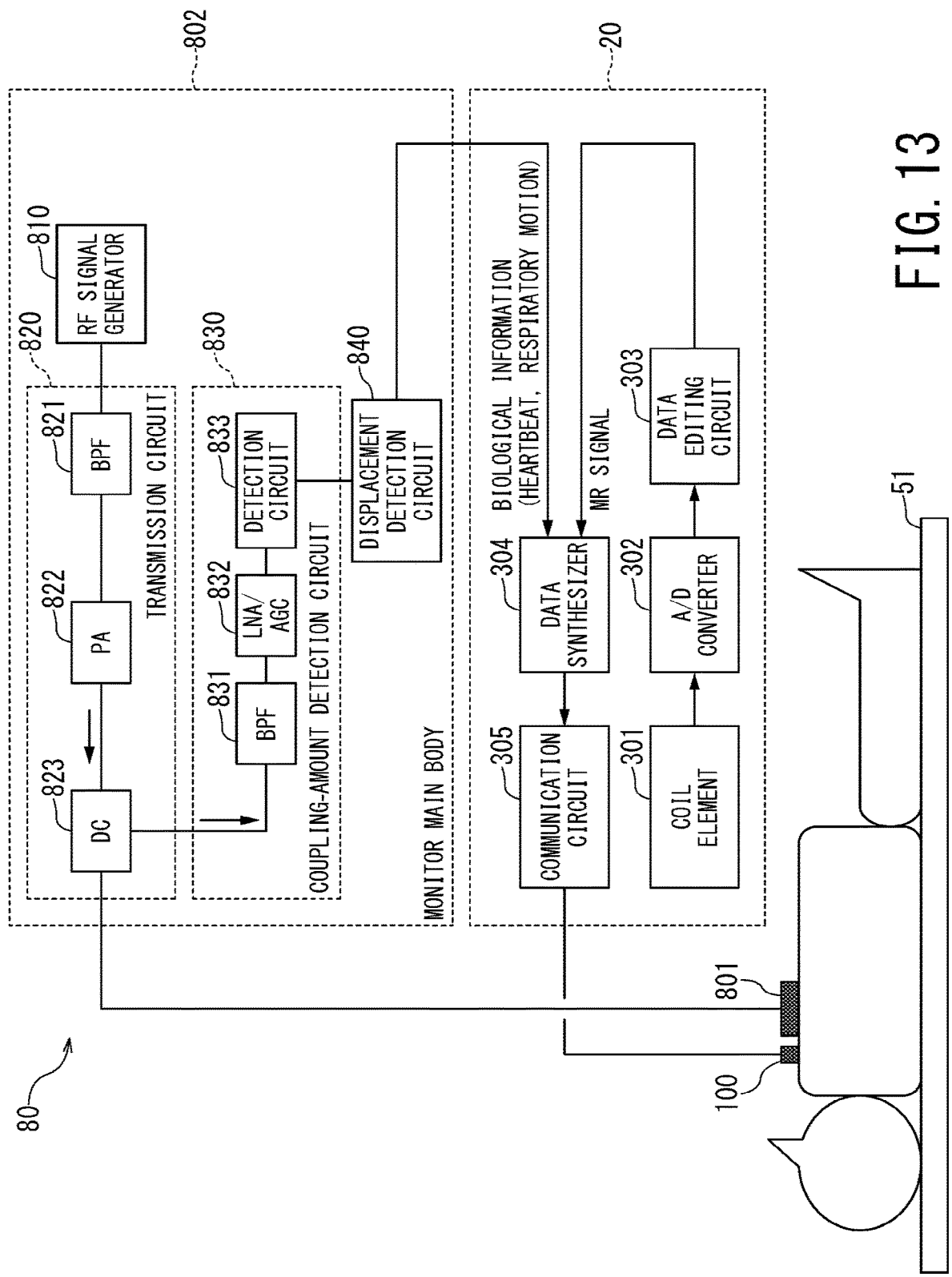
FIG. 13 is a block diagram illustrating a configuration of an RF coil provided with a biological information monitor.

FIG. 13 is a block diagram illustrating the configuration of the RF coil 20 that is provided with the biological information monitor 80. The biological information monitor 80 includes a monitor main body 802 and at least one biological-information monitoring antenna 801 (hereinafter simply referred to as the monitoring antenna 801) disposed in the vicinity of the object.

The monitor main body 802 includes: an RF signal generator 810; a transmission circuit (or, transmitter) 820, a coupling-amount detection circuit (or, coupling-amount detector) 830, and a displacement detection circuit (displacement detector) 840.

The RF signal generator 810 generates a high-frequency signal as a continuous wave. Although the frequency of the high-frequency signal is not particularly limited, the frequency of the VHF band or the UHF band is selected from the viewpoint of the dimensions of the monitoring antenna 801, for example.

The transmission circuit 820 causes the high-frequency signal to pass through a band-pass filter (BPF) 821, then amplifies it to a predetermined power by a power amplifier (PA) 822, and then transmits it to the monitoring antenna 801 via a directional coupler (DC) 823.

The coupling-amount detection circuit 830 has a function of detecting the coupling amount of near-field coupling due to the electric field between the object and the monitoring antenna 801. For example, the coupling-amount detection circuit 830 includes: a band pass filter (BPF) 831; a low noise amplifier (LNA/AGC) 832 with an automatic gain control function; and a detection circuit 833.

Although the high-frequency signal outputted from the directional coupler 823 of the transmission circuit 820 is inputted to the monitoring antenna 801, part of this high-frequency signal does not go into the object but is bounced off (i.e., reflected) at the input end of the monitoring antenna 801 so as to be returned to the directional coupler 823 and then is branched and inputted to the coupling-amount detection circuit 830.

The coupling-amount detection circuit 830 measures the intensity of the reflected signal from the monitoring antenna 801 by causing the detection circuit 833 to detect the signal outputted from the branch end of the directional coupler 823. The coupling-amount detection circuit 830 detects the coupling amount of near-field coupling on the basis of the intensity of the reflected signal.

Considering that the power outputted from the transmission circuit 820 to the monitoring antenna 801 is a constant value, the coupling-amount detection circuit 830 equivalently detects the S11 parameter indicative of the reflection loss (i.e., return loss) of the monitoring antenna 801.

Figure 14B:
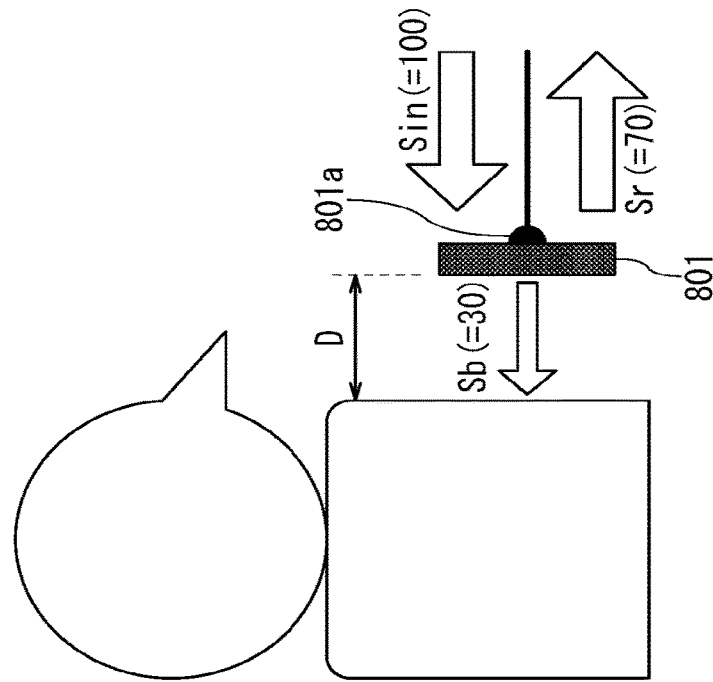
FIG. 14A and FIG. 14B are schematic diagrams illustrating an operation concept of the biological information monitor.
Figure 14A:
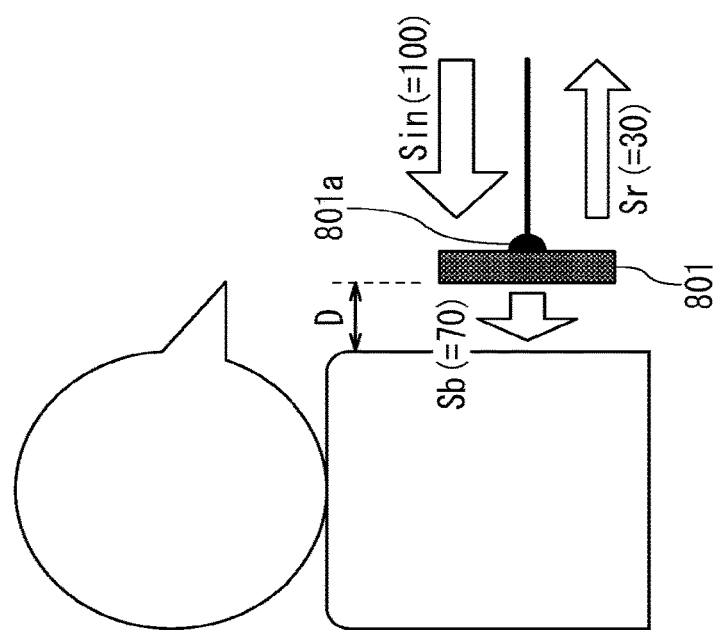

FIG. 14A and FIG. 14B are schematic diagrams illustrating an operation concept of the biological information monitor 80. FIG. 14A schematically illustrates the operation concept when the distance D between the object and the monitoring antenna 801 is short, while FIG. 14B schematically illustrates the operation concept when the distance D between the object and the monitoring antenna 801 is long. The object (human body) is an object having conductivity. Accordingly, the closer the monitoring antenna 801 approaches the object, the more readily the object (human body) absorbs energy from the monitoring antenna 801.

Thus, as shown in FIG. 14A, when the distance D between the object and the monitoring antenna 801 is short, the energy to be absorbed by the object increases. This means that the coupling-amount of near-field coupling between the object and the monitoring antenna 801 is large. Note that the power $S_{in}$ inputted to the monitoring antenna 801 is mainly divided into power Sb absorbed by the object and power Sr reflected from the antenna end 801a of the monitoring antenna 801. When the distance D is short, the power Sb absorbed by the object increases and the power Sr reflected from the antenna end 801a decreases by the increment of the absorbed power Sb. For example, when the power Sin inputted to the monitoring antenna 801 is assumed to be 100, the power Sb absorbed by the object becomes 70 and the power Sr reflected from the antenna end 801a becomes 30.

This means that the reflected signal from the antenna end 801a decreases and the reflection loss (i.e., return loss) of the monitoring antenna 801 also decreases when the distance D between the object and the monitoring antenna 801 is short. In other words, the S11 parameter, which is an index of the degree of mismatch of the monitoring antenna 801, shows a small value. Here, the S11 parameter is an index expressed by the square root of the ratio of the reflected power to the input power to the monitoring antenna 801.

Conversely, as shown in FIG. 14B, when the distance D between the object and the monitoring antenna 801 is long, the energy absorbed by the object is small. This means that the coupling amount of near-field coupling between the object and the monitoring antenna 801 is small. Consequently, when the distance D is long, the power Sb absorbed by the object decreases and the power Sr reflected from the antenna end 801a increases by the decrement of the absorbed power Sb. For example, when the power Sin inputted to the monitoring antenna 801 is assumed to be 100, the power Sb absorbed by the object becomes 30 and the power Sr reflected from the antenna end 801a becomes 70.

This means that the reflected signal from the antenna end 801a increases and the reflection loss (or, return loss) of the monitoring antenna 801 also increases when the distance D between the object and the monitoring antenna 801 is long. In other words, the S11 parameter, which is an index of the degree of mismatch of the monitoring antenna 801, shows a large value.

As described above, when the input power to the monitoring antenna 801 is constant, the reflected signal from the antenna end 801a changes depending on the distance D between the object and the monitoring antenna 801. In other words, the degree of mismatch of the monitoring antenna 801 or the value of the S11 parameter also changes depending on the distance D between the object and the monitoring antenna 801. Since the distance D between the object and the monitoring antenna 801 changes depending on body motions such as heartbeat and/or respiration, the intensity of the reflected signal from the antenna end 801*a* or the value of the S11 parameter changes depending on change in body motion such as heartbeat and/or respiration.

The biological information monitor 80 added to the RF coil 20 utilizes such characteristics and detects a body motion such as heartbeat and/or respiration by detecting the intensity of the reflected signal from the monitoring antenna 801 disposed in the vicinity of the object or the value of the S11 parameter.

As shown in the lower part of FIG. 13, the RF coil 20 includes: coil elements 301; an A/D converter 302; a data editing circuit 303; a data synthesizer 304, and a communication circuit 305.

The MR signal received by the coil elements 301 is converted into a digital signal by the A/D converter 302, then converted by the data editing circuit 303 into data having a data format suitable for transmission to the MRI main body 600, and then inputted to the data synthesizer 304. Meanwhile, the biological information related to a body motion such as heartbeat and/or respiratory motion detected by the biological information monitor 80 is also inputted to the data synthesizer 304. Afterward, the biological information and the MR signal are converted into a predetermined wireless data format by the communication circuit 305, and then transmitted from the coil-side wireless antenna 100 toward the main-body-side wireless antenna 200.

Figure 15A:
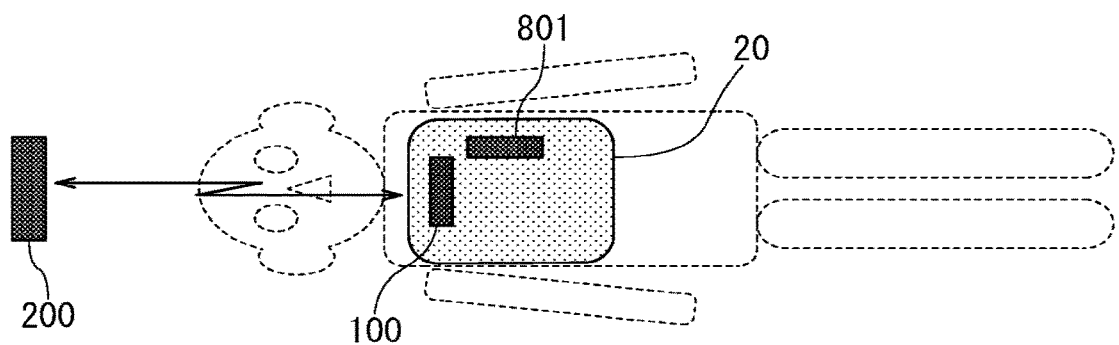
FIG. 15A to FIG. 15C are schematic diagrams illustrating disposition of the coil-side wireless antenna and a monitoring antenna.
Figure 15B:
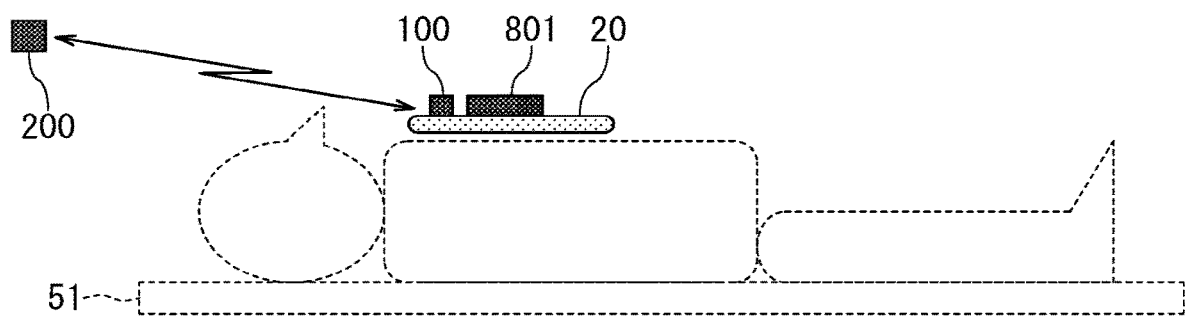
Figure 15C:
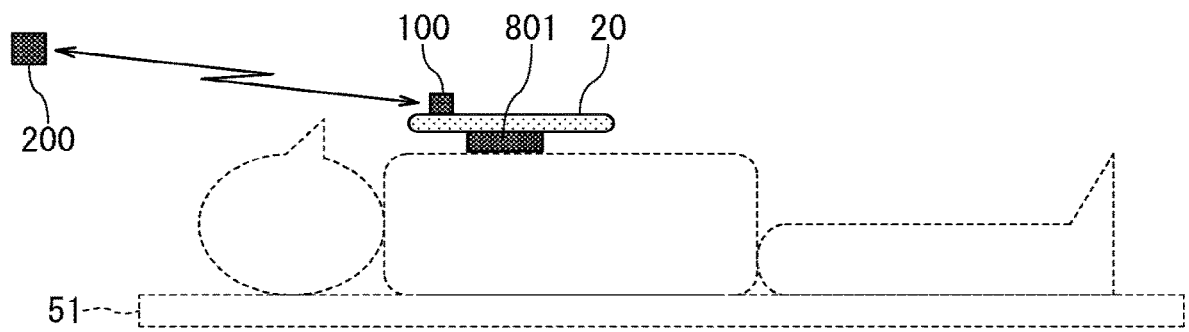

FIG. 15A to FIG. 15C are schematic diagrams illustrating disposition of the coil-side wireless antenna 100 and the monitoring antenna 801. The type of the monitoring antenna 801 can be, for example, a dipole antenna similarly to the coil-side wireless antenna 100. In this case, as shown in FIG. 15A to FIG. 15C, disposing the monitoring antenna 801 orthogonal to the coil-side wireless antenna 100 reduces the coupling between these two antennas.

As shown in FIG. 15B, the monitoring antenna 801 may be disposed on the same side as the coil-side wireless antenna 100 (on the face far from the object). Alternatively, as shown in FIG. 15C, the monitoring antenna 801 may be disposed on the face opposite to the coil-side wireless antenna 100 (on the face closer to the object). In terms of sensitivity of the biological information, it is preferred that the monitoring antenna 801 is disposed on the face closer to the object as shown in FIG. 15C.

Figure 16:
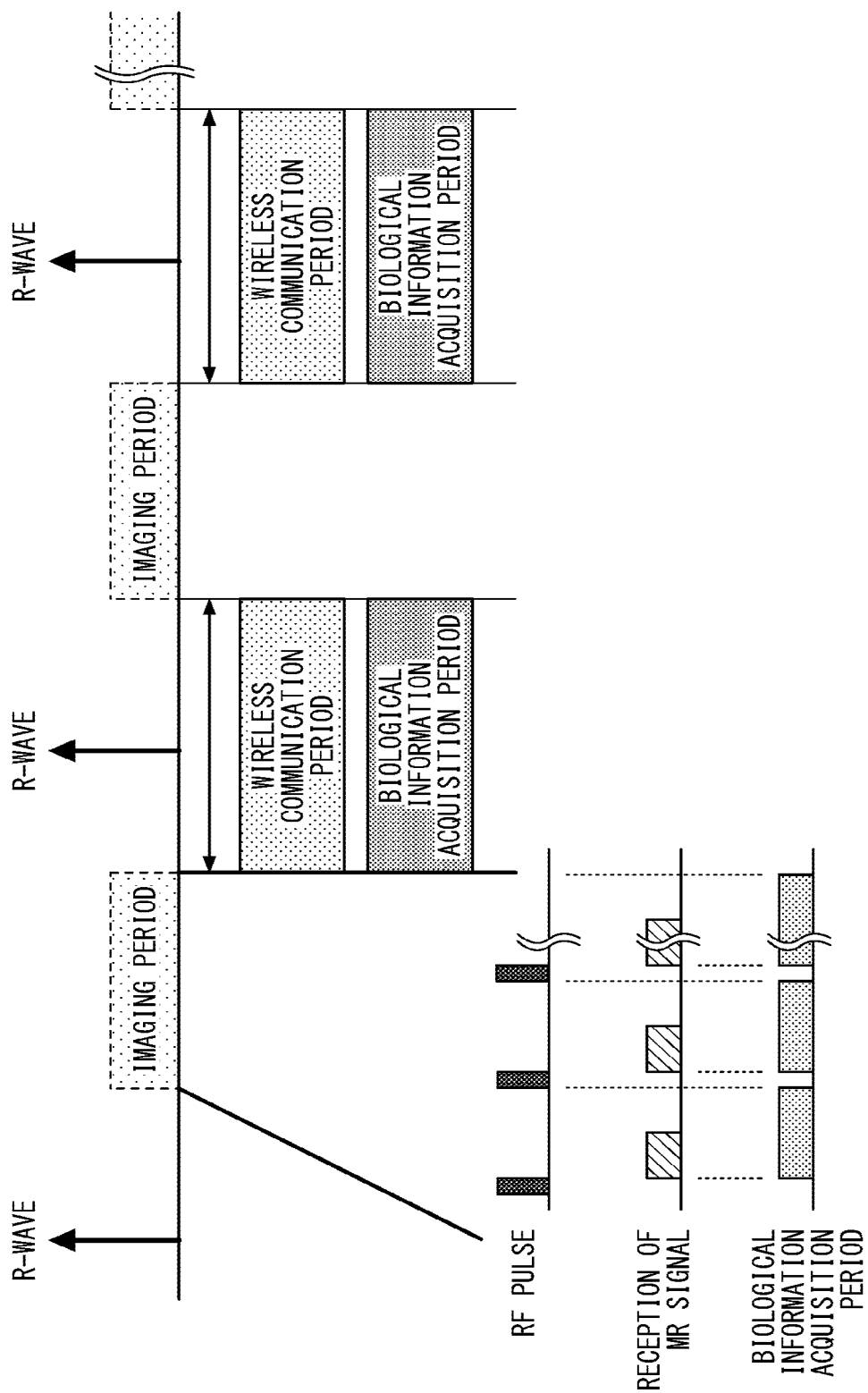
FIG. 16 is a timing chart illustrating first timing relationship between an imaging period, a wireless communication period, and a biological information acquisition period.

FIG. 16 is a timing chart illustrating the first timing relationship between the imaging period in the MRI apparatus 1, and the wireless communication period and the biological information acquisition period. The biological information acquisition period is a period in which biological information such as heartbeat and/or a respiratory motion of the object is acquired by using the above-described biological information monitor 80. The first timing relationship is determined in such a manner that the transmission period of an RF pulse, which has high power, is not superimposed over any part of the wireless communication period or any part of the biological information acquisition period.

The transmission frequency of each RF pulse is defined by the Larmor frequency, and the frequency of the wireless communication and the frequency of the transmission signal for biological monitoring are selected so as to be different from the Larmor frequency in order to avoid interference with each other. Further, the frequency of the wireless communication and the frequency of the transmission signal for biological monitoring are also selected so as to be different from each other in order to avoid interference between both. For example, the 2.4 GHz band or the 5 GHz band is selected as the wireless communication frequency as described above. Meanwhile, as to the frequency of the transmission signal for biological monitoring, for example, a frequency is selected from the VHF band or the UHF band, either of which is higher than the Larmor frequency, and does not match the harmonic of the Larmor frequency.

As described above, the transmission frequency of the RF pulse, the radio communication frequency, and the frequency of transmission signal for biological monitoring are different from each other in terms of avoiding interference. However, the transmission power of the RF pulse is very large. Thus, if the transmission period of the RF pulse is superimposed over some part of the reception period in the wireless communication, there is a possibility of damaging the communication circuit. Hence, during the transmission period of the RF pulse, the antenna end of the communication circuit is opened in order to protect the communication circuit, for example. Similarly, if the transmission period of the RF pulse is superimposed over some part of the reception period of the biological monitoring signal, there is a possibility of damaging the biological information monitor 80, and thus the communication circuit is protected, for example, by opening the antenna end of the biological information monitor 80.

Accordingly, the first timing relationship is determined in such a manner that the transmission period of the RF pulse (included in the imaging period shown in FIG. 16) is not superimposed over any part of the radio communication period or any part of the biological information acquisition period. In the first timing relationship, wireless communication is not performed during the imaging period, and each MR signal acquired during the imaging period is stored in the memory in the RF coil 20. Afterward, during the idle or vacant period from the end of one imaging period to the start of the subsequent imaging period, the stored MR signal is wirelessly transmitted from the RF coil 20 to the MRI main body 600.

During the imaging period, the biological monitoring signal is acquired at a timing that is not superimposed over any part of the transmission period of the RF pulse, and then is stored in the memory in the RF coil 20 in the same manner as the MR signals. Afterward, during the vacant period from the end of one imaging period to the start of the subsequent imaging period, the stored biological signal is wirelessly transmitted from the RF coil 20 to the MRI main body 600 similarly to the case of the MR signal. The biological monitoring signals may be acquired even during the vacant period from the end of one imaging period to the start of the subsequent imaging period. The biological monitoring signal acquired during the vacant period may be transmitted from the RF coil 20 to the MRI main body 600 in real time.

The first timing relationship shown in FIG. 16 is effective in the case of an imaging method in which time-divided imaging can be performed as in an electrocardiographic synchronization imaging using R waves and a vacant period can be provided between one imaging period and the subsequent imaging period, for example. However, the first timing relationship is not suitable for an imaging method in which acquisition of an MR signal is continuously performed asynchronously with the R-wave. Even in the electrocardiogram synchronization method, the first timing relationship is not suitable for an imaging method in which acquisition of an MR signal is continuously performed over a plurality of R-waves. Thus, there is a demand for an antenna that can continuously perform wireless communication regardless of whether an RF pulse is applied or not.

Figure 17B:
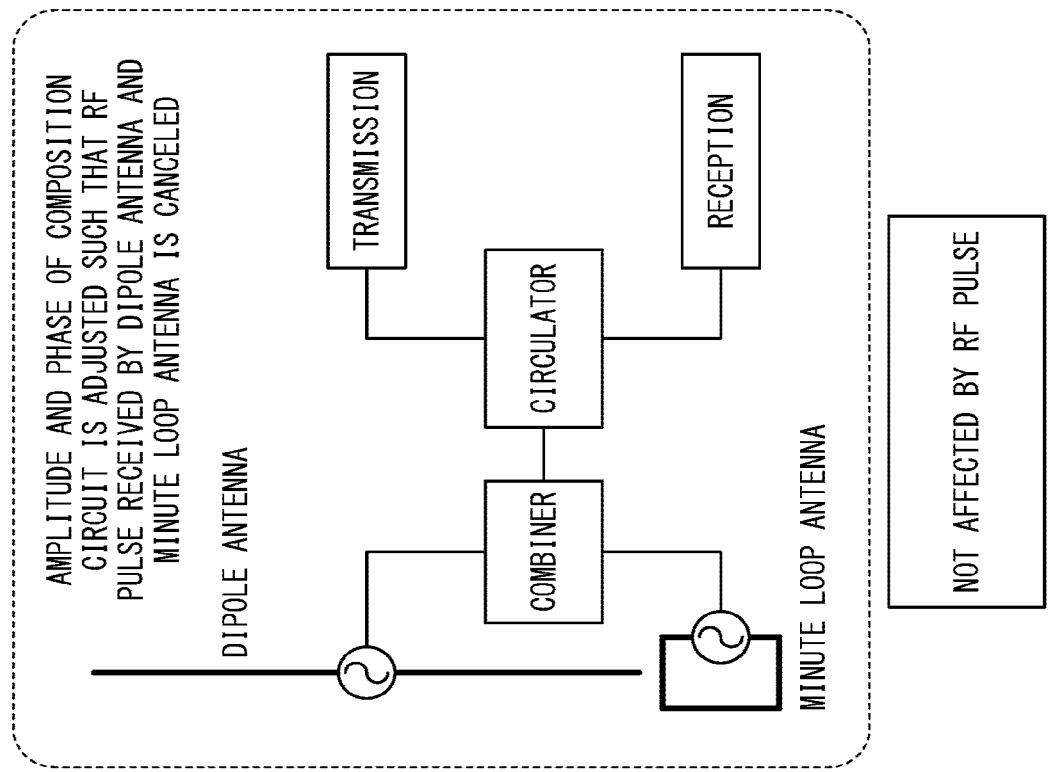
FIG. 17A and FIG. 17B are schematic diagrams illustrating an antenna configured to suppress an induced signal attributable to application of an RF pulse.
Figure 17A:
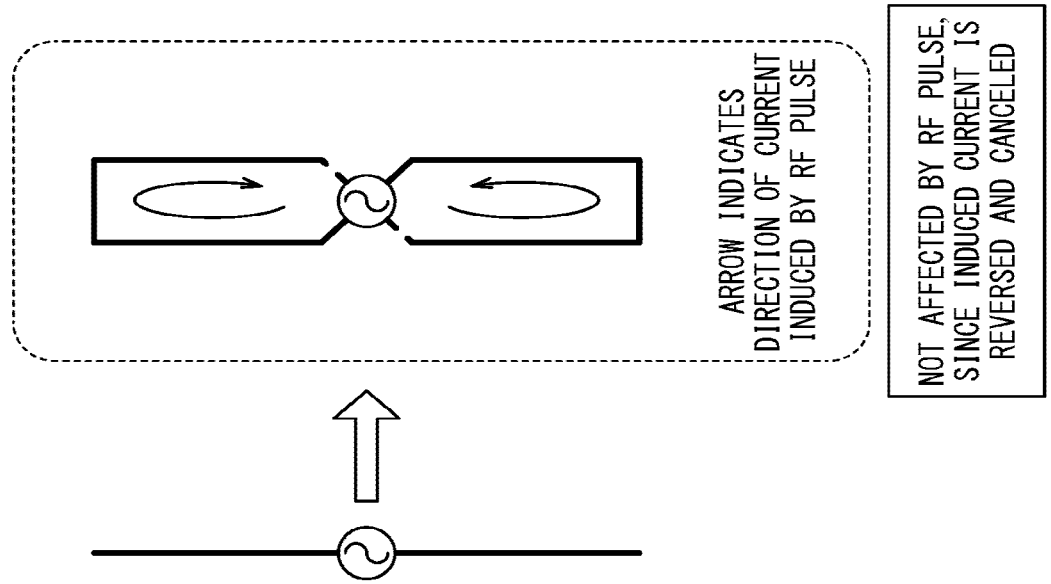

FIG. 17A and FIG. 17B are schematic diagrams illustrating an antenna that is configured to suppress an induced signal due to application of an RF pulse for meeting such a demand. The antenna shown in FIG. 17A is an antenna having a structure in which a loop antenna is twisted. In this twisted loop antenna, the portion indicated by the broken line in the feeding portion is formed on the back face of the dielectric substrate, the other portion indicated by the solid line is formed on the front face of the dielectric substrate, and the broken-line portion on the back face and the solid-line portion on the front face are connected by a through hole. With such a structure, the direction of the induced current caused by the RF pulse is reversed between one loop and the other loop, so the induced current is canceled.

When such a twisted loop antenna is used as an antenna for wireless communication (the coil-side wireless antenna 100 and the main-body-side wireless antennas 200), the influence of the RF pulse is suppressed, and the wireless circuit can be prevented from being damaged by an RF pulse. Thus, wireless communication can be continued even during a transmission period of an RF pulse. Further, when such a twisted loop antenna is used as the monitoring antenna 801 of the biological information monitor 80, monitoring of biological information can be continued even during a transmission period of an RF pulse.

FIG. 17B illustrates another antenna configured to suppress an induced signal caused by application of an RF pulse. This antenna includes a minute loop antenna in addition to the dipole antenna and combines the output of the dipole antenna and the output of the minute loop antenna by a combining circuit. The output of the combining circuit is inputted to the reception circuit via a circulator. The dipole antenna and the minute loop antenna are caused to receive an RF pulse in advance and this reception result is used for adjusting the amplitude and phase of the signal received by the minute loop antenna such that the respective signals received by both antennas are canceled at the output of the combining circuit.

This configuration and adjustment enable the antenna to prevent the signal of the RF pulse from flowing into the reception circuit and the transmission circuit during wireless communication. Since the minute loop antenna is not matched to the frequency of wireless communication and the frequency of an RF pulse, the minute loop antenna does not contribute to transmission/reception of wireless communication signals and reception of MR signals. However, the transmission power of the RF pulse is so large that the minute loop antenna receives the RF pulse with a certain amount of power despite being unmatched to the RF pulse, and the minute loop antenna adjusts the signal of the RF pulse so as to cancel the RF pulse at the output of the combining circuit.

The combining circuit may be configured such that the combining circuit operates only at the time of transmission of an RF pulse and the output of the dipole antenna is connected to the circulator by bypassing the combining circuit during all the other periods.

Instead of the minute loop antenna, it may be configured to cancel the RF pulse at the output of the combining circuit by using the signals of the coil elements of the RF coil 20. Although the coil elements of the RF coil 20 are configured to be unexcited at the time of transmission of an RF pulse, the RF pulse is slightly excited in the ground in the RF coil 20 at the time of transmission of the RF pulse. When it is configured such that this excited RF pulse is inputted to the combining circuit, the signal of the RF pulse entering the circulator from the dipole antenna can be canceled.

When the above-described antenna configured to suppress the induced signal due to the application of the RF pulse is used as an antenna for wireless communication (i.e., the coil-side wireless antenna 100 and the main-body-side wireless antennas 200), the wireless circuit can be prevented from being damaged by the RF pulse and the wireless communication can be continued during the transmission period of the RF pulse.

Figure 18:
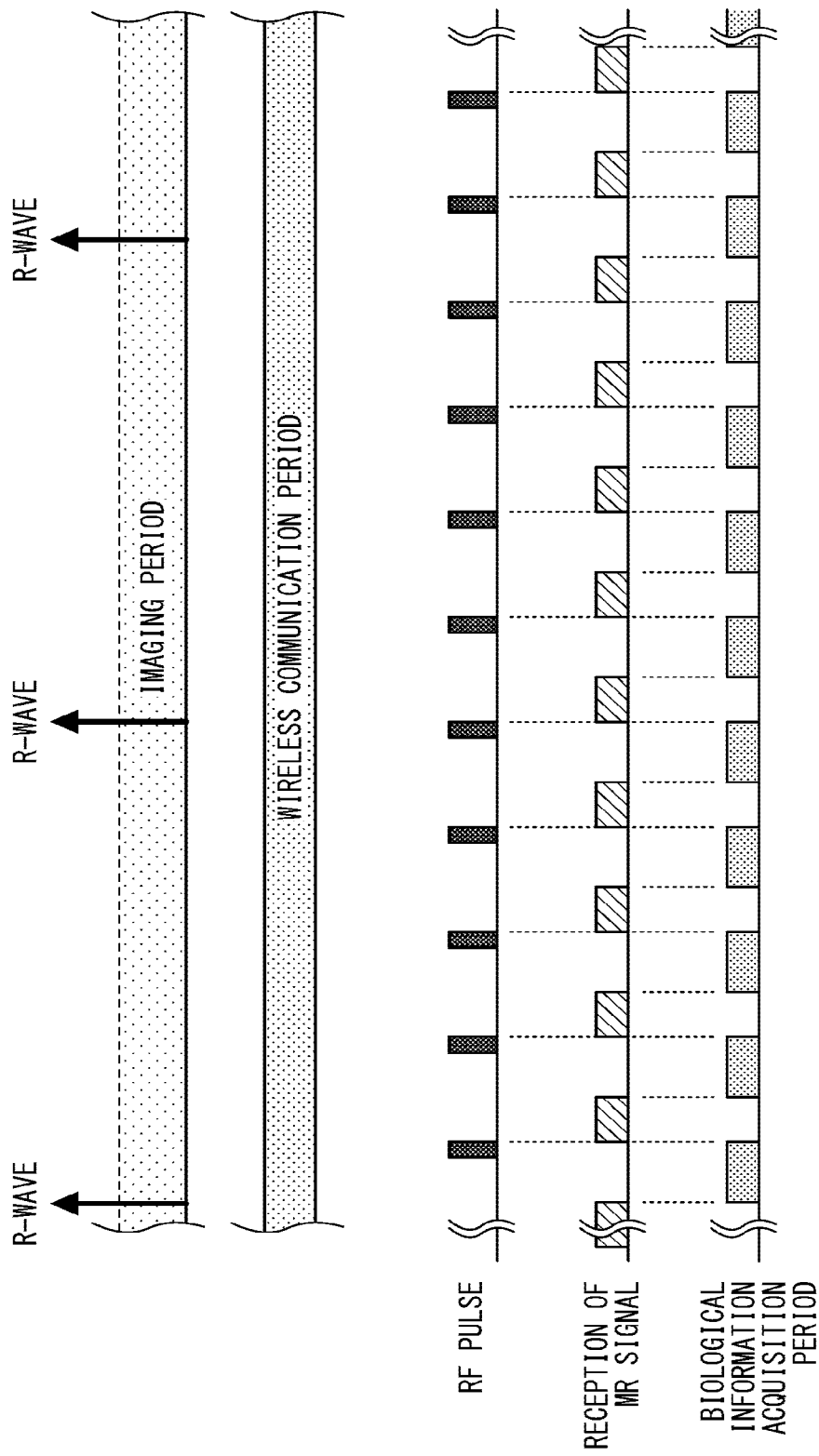
FIG. 18 is a timing chart illustrating second timing relationship in which the imaging period and the wireless communication period can be set to be continuous regardless of the biological information acquisition period (i.e., MR signals can be continuously transmitted wirelessly regardless of whether an RF pulse is applied or not).

FIG. 18 is a timing chart illustrating the second timing relationship in which MR signals or both of MR signals and biological information can be continuously transmitted wirelessly regardless of whether an RF pulse is applied or not. In the second timing relationship, as shown in the top part and the second top part of FIG. 18, even when acquisition of the MR signal is continuously performed, wireless communication can be continued regardless of whether the RF pulse is applied or not.

Further, when the above-described antenna configured to suppress the induced signal due to the application of the RF pulse is used as the monitoring antenna 801 of the biological information monitor 80, acquisition of biological information can be continued during the transmission period of the RF pulse. However, as shown in the bottom part of FIG. 18, when biological information is acquired by avoiding the reception period of each MR signal, the concern about interference with the MR signal can be eliminated.

According to the MRI apparatus 1 of each embodiment described above, in an MRI apparatus having a wireless RF coil, a stable wireless communication line between the RF coil and the main body of the MRI apparatus can be secured. In addition, biological information such as heartbeat and respiration of the object can be readily acquired without imposing a burden on the object.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An MRI apparatus comprising:
 a first RF coil configured as a surface coil to receive a magnetic resonance signal from an object and include a first wireless antenna, wherein the first wireless antenna is mounted or accommodated along a main face of the surface coil and exhibits horizontal polarization when the surface coil is horizontally placed on the object;
 a main body provided with a bore and including a second RF coil configured to apply an RF pulse to the object, the bore being a space in which the object is placed during imaging; and
 at least one second wireless antenna configured to perform wireless communication with the first RF coil via the first wireless antenna, one of the at least one second wireless antenna being disposed at an uppermost portion in a circumference of an open end of the bore.

2. The MRI apparatus according to claim 1, wherein the first wireless antenna is disposed in such a manner that a main beam direction of the first wireless antenna is in a direction toward the open end of the bore.

3. The MRI apparatus according to claim 1, wherein the first wireless antenna is a dipole antenna or a monopole antenna, and the first wireless antenna is housed inside the first RF coil or is mounted outside the first RF coil.

4. The MM apparatus according to claim 1, wherein the first wireless antenna is configured as an endfire array antenna having directivity in a direction toward the open end of the bore.

5. The MRI apparatus according to claim 1, wherein the first wireless antenna is configured as a Multiple-Input and Multiple-Output (MIMO) antenna that can be controlled in directivity.

6. The MRI apparatus according to claim 1, wherein the second wireless antenna is configured as a polarization diversity antenna that includes a dipole antenna and a slot antenna.

7. The MRI apparatus according to claim 6, wherein the dipole antenna and the slot antenna are disposed in such a manner that an element of the dipole antenna and a slot of the slot antenna are arranged in parallel and side-by-side.

8. The MRI apparatus according to claim 7, wherein:
the slot antenna is disposed in such a manner that a conductor plate surrounding the slot is substantially orthogonal to a longitudinal direction of the bore; and
the dipole antenna is disposed at a position where a distance between the dipole antenna and the first wireless antenna is shorter than the distance between the slot antenna and the first wireless antenna, and wherein the dipole antenna is close to the slot antenna to such an extent that the conductor plate of the slot antenna functions as a reflector of the dipole antenna.

9. The MRI apparatus according to claim 6, wherein the slot antenna is configured as a slot antenna with a cavity resonator.

10. The MRI apparatus according to claim 6, wherein the at least one second wireless antenna constitutes the polarization diversity antenna at a time of reception by adding a reception signal of the dipole antenna and a reception signal of the slot antenna, wherein the reception signal of the dipole antenna and the reception signal of the slot antenna have a same weight when being added.

11. The MRI apparatus according to claim 6, wherein the at least one second wireless antenna is configured to operate during transmission in such a manner that the at least one second wireless antenna feeds the dipole antenna by weighting a transmission signal with a first weight and feeds the slot antenna by weighting the transmission signal with a second weight; and the first weight and the second weight are values adjusted to maximize a composite signal of a reception signal of the dipole antenna after weighting and a reception signal of the slot antenna after weighting when a signal from the first wireless antenna is received by the at least one second wireless antenna at a position where the second wireless antenna is disposed.

12. The MM apparatus according to claim 1, further comprising a housing configured to house the at least one second wireless antenna, wherein: the bore is formed in a cylindrical shape; and one side face of the housing is formed in an arc shape that conforms to a shape of an outer peripheral face of the bore.

13. The MRI apparatus according to claim 1, wherein:
the at least one second wireless antenna comprises a plurality of second wireless antennas; and the plurality of second wireless antennas are disposed at an outer periphery of the open end of the bore in such a manner that the plurality of second wireless antennas are disposed in a left-right asymmetric manner except one second wireless antenna disposed at the uppermost portion.

14. The MRI apparatus according to claim 1, wherein: the at least one second wireless antenna comprises a plurality of second wireless antennas; and the plurality of second wireless antennas are disposed at half-wavelength intervals along an outer periphery of the open end of the bore and are configured to be selectable in position and number from among the plurality of second wireless antennas.

15. An MRI apparatus, comprising:
a first RF coil configured to receive a magnetic resonance signal from an object and include a first wireless antenna with horizontal polarization;
a main body provided with a bore and including a second RF coil configured to apply an RF pulse to the object, the bore being a space in which the object is placed during imaging;
at least one second wireless antenna configured to perform wireless communication with the first RF coil via the first wireless antenna, one of the at least one second wireless antenna being disposed at an uppermost portion in an outer periphery of an open end of the bore; and
a biological information monitor that is connected to the first RF coil and is configured to detect biological information of the object,
wherein
the biological information detected by the biological information monitor is wirelessly transmitted between the first wireless antenna and the at least one second wireless antenna; and
wherein the biological information monitor includes
at least one biological-information monitoring antenna disposed close to the object,
a signal generator configured to generate a high-frequency signal,
a coupling-amount detector configured to detect coupling amount of near-field coupling due to an electric field between the object and the biological information monitoring antenna by using the high-frequency signal, and
a displacement detector configured to detect biological information of the object by detecting a physical displacement of the object based on change in coupling amount of the near-field coupling.

16. The MRI apparatus according to claim 15, wherein the biological-information monitoring antenna is disposed at one face of the first RF coil or an opposite face of the first RF coil, the one face being on a side of the object, the opposite face being on an opposite side of the object.

17. The MRI apparatus according to claim 16, wherein the biological-information monitoring antenna is disposed in such a manner that a longitudinal direction of an element of the biological-information monitoring antenna becomes substantially orthogonal to a longitudinal direction of an element of the first wireless antenna.

18. An MRI apparatus comprising:
a first RF coil configured to receive a magnetic resonance signal from an object and include a first wireless antenna with horizontal polarization;

a main body provided with a bore and including a second RF coil configured to apply an RF pulse to the object, the bore being a space in which the object is placed during imaging; and at least one second wireless antenna configured to perform wireless communication with the first RF coil via the first wireless antenna, one of the at least one second wireless antenna being disposed at an uppermost portion in an outer periphery of an open end of the bore, wherein:

the first wireless antenna and the at least one second wireless antenna are antennas configured to suppress an induced signal caused by application of the RF pulse; and the first RF coil is configured to perform wireless communication between the first wireless antenna and the at least one second wireless antenna in such a manner that the magnetic resonance signal received by the first RF coil is continuously transmitted from the first RF coil to the at least one second wireless antenna regardless of whether or not the RF pulse is applied.

19. The MRI apparatus according to claim 15, wherein:

the first wireless antenna and the at least one second wireless antenna are antennas configured to suppress an induced signal caused by application of the RF pulse; and the first RF coil is configured to perform wireless communication between the first wireless antenna and the at least one second wireless antenna in such a manner that the magnetic resonance signal received by the first RF coil and the biological information detected by the biological information monitor are continuously transmitted from the first RF coil to the at least one second wireless antenna regardless of whether or not the RF pulse is applied.

20. The MRI apparatus according to claim 15, wherein the biological-information monitoring antenna is configured to suppress an induced signal caused by application of the RF pulse.

* * * * *